United States Patent [19]
Tu et al.

[11] Patent Number: 5,945,527
[45] Date of Patent: *Aug. 31, 1999

[54] PALLADIUM CATALYZED NUCLEOSIDE MODIFICATION METHODS USING NUCLEOPHILES AND CARBON MONOXIDE

[75] Inventors: Chi Tu, Louisville; Torin Dewey; Bruce Eaton, both of Boulder, all of Colo.

[73] Assignee: NeXstar Pharmaceuticals, Inc., Boulder, Colo.

[*] Notice: This patent is subject to a terminal disclaimer.

[21] Appl. No.: 08/952,338

[22] PCT Filed: May 30, 1996

[86] PCT No.: PCT/US96/08026

§ 371 Date: Nov. 4, 1997

§ 102(e) Date: Nov. 4, 1997

[87] PCT Pub. No.: WO96/38460

PCT Pub. Date: Dec. 5, 1996

[51] Int. Cl.$^6$ ..................................................... C07H 19/00
[52] U.S. Cl. ................. 536/27.6; 536/27.61; 536/27.62; 536/27.8; 536/27.81; 536/28.5; 536/28.51; 536/28.52; 536/28.53; 536/28.54; 536/28.55
[58] Field of Search ............................... 536/27.6, 27.61, 536/27.62, 27.8, 28.5–28.55

[56] References Cited

U.S. PATENT DOCUMENTS

| | | |
|---|---|---|
| 5,047,519 | 9/1991 | Hobbs, Jr. et al. . |
| 5,053,449 | 10/1991 | Kojima et al. . |
| 5,420,276 | 5/1995 | Norbeck . |
| 5,428,149 | 6/1995 | Eaton . |
| 5,580,972 | 12/1996 | Tu et al. . |

FOREIGN PATENT DOCUMENTS

| | | |
|---|---|---|
| WO 90/15065 | 12/1990 | WIPO . |
| WO 91/06556 | 5/1991 | WIPO . |
| WO 91/06629 | 5/1991 | WIPO . |
| WO 91/10671 | 7/1991 | WIPO . |
| WO 91/14696 | 10/1991 | WIPO . |
| WO 94/26761 | 11/1994 | WIPO . |
| WO 94/29279 | 12/1994 | WIPO . |

OTHER PUBLICATIONS

Crisp and Flynn (1990) Tetrahedron Letters 31:1347.
Sentemov et al. (1991) Chemical Abstract 115:92415h.
*Comp. Organomet. Chem.* (1982) 6:1003, Wilkinson, Stone & Abel, Editors, Pergamon Press.
Agathocleous and Shaw (1991) J. Chem. Soc. Perkins Trans. 1 pp . 2317–2321.
Arai and Daves, Jr. (1978) J. Am. Chem. Soc. 100:287.
Bergstrom et al. (1981) J. Org. Chem. 46:1432.
Bergstrom and Ruth (1976) J. Am. Chem. Soc. 98:1587.
Bergstrom et al. (1982) J. Org. Chem. 47:2174.
Crisp (1989) Syn. Commun. 19:2117.
Crouch and Eaton (1994) Nucleosides and Nucleotides 13:939–944.
Dreyer and Dervan (1985) Proc. Natl. Acad. Sci. USA 82:968.
Fukuda et al. (1986) Z. for Naturforschung 41b:1571.
Guschlbauer et al. (1977) Nucleic Acids Research 4:1933.
Hacksell and Daves, Jr. (1983) J. Org. Chem. 48:2870.
Hobbs et al. (1973) Biochemistry 12:5138.
Ikehara and Tada (1968) in *Synthetic Procedures in Nucleic Acid Chemistry*, Zorbach, W.W.; Tipson, R.S. Eds.; John Wiley and Sons, NY, pp. 188–192.
Ono et al. (1994) Bioorganic & Medicinal Chem. Letters 4:361.
Pieken et al. (1991) Science 253:314.
Ruth and Bergstrom (1978) J. Org. Chem. 43:2870.
Sagi et al (1994) J. Med. Chem. 37:1307.
Sessler et al. (1993) J. Am. Chem. Soc. 115:10418.
Shibahara et al. (1987) Nucleic Acids Research 15:4403.
Sproat et al. (1989) Nucleic Acids Research 17:3373.
Tronchet et al. (1988) Nucleosides & Nucleotides 7:249.
Van Aerschot et al. (1993) J. Med. Chem. 36:2938.
Zhang and Daves, Jr. (1993) Organometallics 12:1499.

*Primary Examiner*—James O. Wilson
*Assistant Examiner*—Howard Owens
*Attorney, Agent, or Firm*—Swanson & Bratschun LLC

[57] ABSTRACT

This invention discloses a method for the preparation modified nucleosides and nucleotides using a palladium catalyst, a nucleophile and carbon monoxide.

28 Claims, No Drawings

PALLADIUM CATALYZED NUCLEOSIDE MODIFICATION METHODS USING NUCLEOPHILES AND CARBON MONOXIDE

FIELD OF THE INVENTION

This invention relates to the field of nucleic acid chemistry, specifically to a process for preparing modified nucleosides. The nucleosides can be pyrimidines or purines. The pyrimidine compounds of the invention can be modified at the 5-, or 6-position of the pyrimidine ring. The purine compounds of the invention can be modified at the 2-, 6- or 8-position of the purine ring. Most preferably, the invention includes a process for preparing 8-position modified purine compounds and 5-position modified pyrimidine compounds. The present invention also includes the modified nucleosides produced by the method. The invention also includes the use of the modified nucleosides as anti-viral, anti-bacterial, anti-fungal or anti-neoplastic agents or as part of an oligonucleotide.

BACKGROUND OF THE INVENTION

Until quite recently, the consideration of oligonucleotides in any function other than strictly informational was not known. Despite the fact that certain oligonucleotides were known to have interesting structural possibilities (e.g., t-RNAs) and other oligonucleotides were bound specifically by polypeptides in nature, very little attention had been focused on the non-informational capacities of oligonucleotides. For this reason, among others, little consideration had been given to using oligonucleotides as pharmaceutical compounds.

There are currently at least three areas of exploration that have led to serious studies regarding the use of oligonucleotides as pharmaceuticals. In the most advanced of the fields, antisense oligonucleotides are utilized to bind to certain regions in an organism to prevent the expression of proteins or to block various cell functions. The discovery of RNA species with catalytic functions—ribozymes—has led to the consideration of RNA species that serve to perform intracellular reactions that will achieve desired effects. And lastly, the discovery of the SELEX process (Systematic Evolution of Ligands by EXponential Enrichment) has shown the research community that oligonucleotides can be identified that will bind to almost any biologically interesting target.

The use of antisense oligonucleotides as a method for controlling gene expression and the potential for using oligonucleotides as pharmaceutical materials has prompted investigations into the introduction of a number of chemical modifications into oligonucleotides to increase their therapeutic activity. Such modifications are designed to increase cell penetration of the oligonucleotides, to stabilize them from nucleases and other enzymes that degrade or interfere with the structure or activity of the oligonucleotide analogs in the body, to enhance their binding to targeted nucleic acids, to provide a mode of disruption (terminating event) once sequence-specifically bound to targeted nucleic acids, and to improve their pharmacokinetic properties. For example, PCT Patent Application Publication WO 91/14696, entitled: Oligonucleotide-Transport Agent Disulfide Conjugates, describes a method for chemically modifying antisense oligonucleotides to enhance entry into a cell.

A variety of methods have been used to render oligonucleotides resistant to degradation by exonucleases. PCT Patent Application Publication WO 90/15065, entitled: Exonuclease-Resistant Oligonucleotides and Methods for Preparing the Same, describes a method for making exonuclease-resistant oligonucleotides by incorporating two or more phosphoramidite and phosphoromonothionate and/or phosphorodithionate linkages at the 5' and/or 3' ends of the oligonucleotide. PCT Patent Application Publication WO 91/06629, entitled: Oligonucleotide Analogs with Novel Linkages, describes oligonucleotide compounds with one or more phosphodiester linkages between adjacent nucleotides replaced by a formacetal/ketal type linkage which are capable of binding RNA or DNA.

A common strategy for stabilization of RNA against endonucleolytic cleavage is to modify the 2'-position of ribonucleotides. Interference with base recognition by enzymes can be used to approach stabilization against base-specific endonucleolytic cleavage. Several strategies for this modification are known, including modification with 2'-amino and 2'-fluoro (Hobbs et al. (1973) Biochemistry 12:5138; Guschlbauer et al. (1977) Nucleic Acids Res. 4:1933), and 2'-OCH$_3$ (Shibahara et al. (1987) 15:4403; Sproat et al. (1989) Nucleic Acids Res. 17:3373). PCT Patent Application Publication WO 91/06556, entitled: 2' Modified Oligonucleotides, describes nuclease-resistant oligomers with substituents at the 2' position. PCT Patent Application Publication WO 91/10671, entitled: Compositions and Methods for Detecting and Modulating RNA Activity and Gene Expression, describes antisense oligonucleotides chemically modified at the 2' position and containing a reactive portion capable of catalyzing, alkylating, or otherwise effecting the cleavage of RNA, a targeting portion, and a tether portion for connecting the targeting and reactive portions.

The 5-position of pyrimidines may also be chemically modified. The introduction of modifications at the C-5 position of pyrimidines may be envisioned to interfere with the recognition by pyrimidine specific endonucleases. However, this concept is not as clear cut as the modification of the 2'-position of ribonucleotides.

The use of palladium to catalyze carbon-carbon bond formation at the 5 position of pyrimidine nucleosides is known. A superior method for 5-position modification of pyrimidines is described in U.S. Pat. No. 5,428,149, entitled "Method for Palladium Catalyzed Carbon-Carbon Coupling and Products," now U.S. Pat. No. 5,428,149, which is herein incorporated by reference in its entirety. The first examples of 5-position pyrimidine modifications were demonstrated by Bergstrom (Bergstrom et al. (1976) J. Am. Chem. Soc. 98:1587, (1978) J. Org. Chem. 43:2870, (1981) J. Org. Chem. 46:1432 and 2870, (1982) J. Org. Chem. 47:2174) and Daves (Arai and Daves (1978) J. Am. Chem. Soc., 100:287; Hacksell and Daves (1983) J. Org. Chem. 48:2870). Bergstrom and Daves used 5-mercurialdeoxyuridine compounds, the same as those used by Dreyer and Dervan ((1985) Proc. Natl. Acad. Sci. USA 82:968), to tether functional groups to oligonucleotides.

One method for simple carbon-carbon coupling reactions to the 5-position of uridines is described in the work of Crisp (1989) Syn. Commun. 19:2117. Crisp forms deoxyuridines functionalized at the 5-position by reacting protected 5-iodo-2'-deoxyuridine with alkenylstannanes in acetonitrile in the presence of a Pd (II) catalyst.

To date, very little work has been done to modify purine nucleosides using palladium catalysis. Van Aerschot et al., ((1993) J. Med. Chem 36:2938–2942) report that 2-, 6-, and 8-halogenated adenosines can be modified with symmetric organotin reagents. However, symmetric organotin compounds are not widely available. Sessler et al., ((1993) J.

Am. Chem. 115:10418–10419) describe the arylation of protected 8-bromoguanosine with 4-tributyltinbenzaldehyde. However, using this procedure, a significant amount of starting material (28%) was unreacted. A superior method for modifying purine nucleosides using palladium catalysts is described in U.S. patent application Ser. No. 08/347,600, filed Dec. 1, 1994, entitled "Purine Nucleoside Modification by Palladium Catalyzed Methods", which is herein incorporated by reference in its entirety.

Additionally, very little work has been done in the area of palladium catalyzed amidations. Schoenberg, et al. (J. Org. Chem. (1974) 39:3327) describe amidation of aryl and alkenyl halides, however, this work does not include nucleoside substrates or the use of a $PdL_4$ catalyst.

SELEX (Systematic Evolution of Ligands for EXponential Enrichment) is a method for identifying and producing nucleic acid ligands, termed "nucleic acid antibodies", e.g., nucleic acids that selectively bind to target molecules (Tuerk and Gold (1990) Science 249:505). The method involves selection from a mixture of candidates and step-wise iterations of structural improvement, using the same general selection theme, to achieve virtually any desired criterion of affinity and selectivity. Starting from a mixture of nucleic acids, the method includes steps of contacting the mixture with the target under conditions favorable for interaction, partitioning non-interacting nucleic acids from those nucleic acids which have interacted with the target molecules, dissociating the nucleic acid-target pairs, amplifying the nucleic acids dissociated from the nucleic acid-target pairs to yield a mixture of nucleic acids enriched for those which interact with the target, then reiterating the steps of interacting, partitioning, dissociating and amplifying through as many cycles as desired.

The methods of the present invention may be combined with SELEX to produce nucleic acids containing modified nucleotides. The presence of modified nucleotides may result in nucleic acids with an altered structure exhibiting an increased capacity to interact with target molecules. The steric and electronic influence of modified nucleosides may also act to prevent nuclease degradation. Incorporation of modified nucleotides into oligonucleotides is well known to those skilled in the art (Dewey, T. et al., J. Amer. Chem. Soc. (1995) 117:8474–8475; Walker G. C. et al., Biochemistry (1975) 14:817–823; Connolly, B. A., pp 155–183 In Oligonucleotides and Analogues: A Practical Approach (1991) (editor F. Eckstein) IRL Press, New York).

BRIEF SUMMARY OF THE INVENTION

The present invention includes a novel method for introducing chemical moieties at various positions of nucleoside rings utilizing a palladium catalyst and a nucleophile and carbon monoxide. Preferably, the modifications are at the 5- or 6-position of a pyrimidine ring or at the 2-, 6-, or 8-positions of the purine ring. Most preferably the modifications are at the 5-position of the pyrimidine ring and at the 8-position of the purine ring. Particularly preferred modifications of the nucleoside ring include the introduction of an amide or ester moiety. For the preferred modifications, the nucleophile is a primary or secondary amine.

This invention includes a reaction scheme for producing a wide variety of modified nucleoside molecules. A key element in the production of the modified nucleosides is the use of a palladium catalyst in conjunction with a nucleophile and carbon monoxide.

More specifically, the invention provides a method for the preparation of a modified nucleoside comprising the steps of reacting a nucleoside starting material containing a leaving group attached to a carbon atom of the nucleoside starting material with a nucleophile and carbon monoxide in the presence of a palladium catalyst; and isolating the modified nucleoside. The modified nucleosides produced by this method are also included in the invention.

This invention further includes a method of preparing stabilized nucleic acids wherein the modified nucleoside is coupled to a sugar modified at the 2'-position or the 3'-position.

The modified nucleosides of the invention have many uses including, but not limited to, use as anti-viral, anti-bacterial, anti-fungal, or anti-neoplastic agents and use as part of an oligonucleotide.

DETAILED DESCRIPTION OF THE INVENTION

The present invention includes a method for modifying a nucleoside ring by reacting a nucleoside starting material with a nucleophile and carbon monoxide in the presence of a palladium catalyst. The invention includes the modifications of both pyrimidines and purines. The pyrimidines have the following structures and conventional numbering:

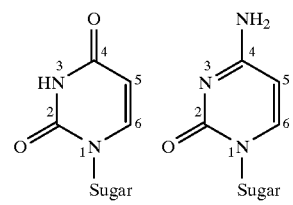

The pyrimidine ring can be modified at the 5- or 6-position; most preferably the 5-position is modified. The purines have the following structures and conventional numbering:

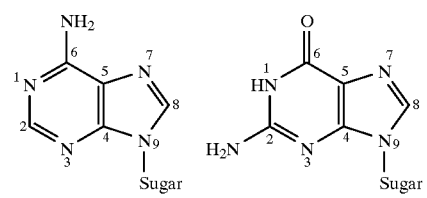

The purine can be modified at positions 2-, 6- and 8- of the purine ring; most preferably the 8-position is modified. Introduction of a variety of modifications to the nucleoside ring are contemplated by this invention. However, particularly preferred modifications to the nucleoside ring include the introduction of an amide or ester moiety. In the preferred modifications, the nucleophile for the carboxyamidation reaction is a primary or secondary amine.

The present invention extends to all novel compounds that can be prepared according to the methods of the present invention. The present invention also includes oligonucleotides that contain one or more of the novel substituted nucleosides of this invention. The present invention also includes the use of the modified nucleosides in various pharmaceutical areas, particularly as anti-virals, anti-bacterials, anti-fungals and anti-neoplastics.

The general reactions of the present invention can be characterized as follows:

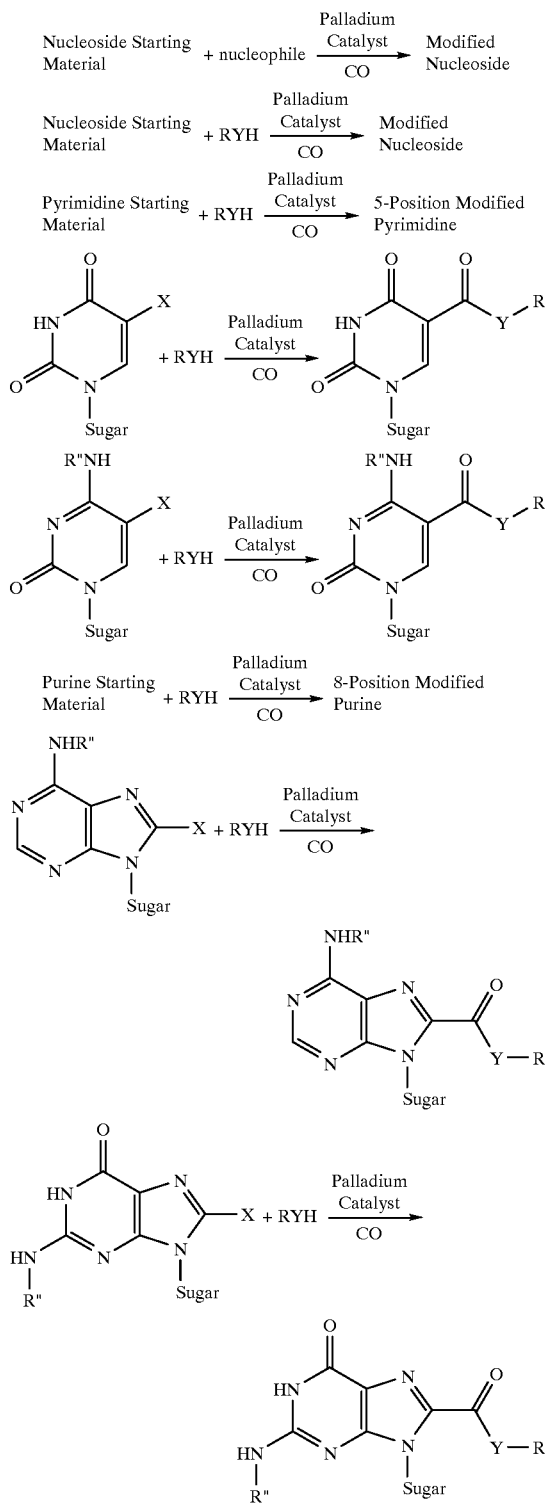

As used herein the term "modified nucleoside" is intended to encompass any nucleoside base, nucleoside, or nucleotide that may be prepared by the method of the present invention. The terms nucleoside base, nucleoside and nucleotide can be used interchangeably herein. The modified nucleosides of the invention can contain various other modifications on the base and sugar.

"Nucleoside starting material" is defined herein as any nucleoside base, nucleoside or nucleotide which has an attached acceptable leaving group (X). Nucleoside starting materials include all nucleosides, both naturally occurring and non-naturally occurring. Preferably, nucleoside starting materials include purines and pyrimidines, which include uracil, thymine, cytosine, adenine and guanine starting materials, or protected derivatives thereof. In certain embodiments, the protected derivatives include those wherein R" is dimethyl formamidine or an acyl group, preferably selected from the group consisting of isobutyryl, acetyl, phenoxyacetyl, and benzoyl. R" is H in unprotected nucleosides. The leaving group can be attached to any free carbon on the nucleoside starting material. The acceptable leaving group is displaced during the catalysis reaction and replaced by C(O)YR chemical moieties to yield the modified base, nucleoside or nucleotide of the invention. The nucleoside starting material can have a sugar moiety attached in the form of a ribose, deoxyribose, dideoxyribose and any combination of 2', 3' or 5' modifications thereof. The invention contemplates the above sugar moieties and any suitable derivatives thereof, such as a ribose or 2'-deoxyribose wherein the hydroxyl groups have been partially or fully protected. For example, the 5'-hydroxyl can be present as the mono-, di-, or tri-phosphate.

"Pyrimidine starting material" is defined herein as a pyrimidine base, pyrimidine nucleoside or pyrimidine nucleotide which has an attached acceptable leaving group (X). Pyrimidine starting materials include all pyrimidines, both naturally occurring and non-naturally occurring. Preferably, pyrimidine starting materials include uracil, thymine, and cytosine, or protected derivatives thereof. The leaving group can be attached to any free carbon on the base of the nucleoside, preferably at the 5- or 6-position. The most preferred attachment is at the 5-position of the pyrimidine ring. The acceptable leaving group is displaced during the catalysis reaction and replaced by C(O)YR chemical moieties to yield the modified pyrimidine. The pyrimidine starting material can have a sugar moiety attached in the form of a ribose, deoxyribose, dideoxyribose and any combination of 2', 3' or 5' modifications thereof. The invention contemplates the above sugar moieties and any suitable derivatives thereof, such as a ribose or 2'-deoxyribose wherein the hydroxyl groups have been partially or fully protected. For example, the 5'-hydroxyl can be present as the mono-, di-, or tri-phosphate.

"Purine starting material" is defined herein as a purine base, purine nucleoside or purine nucleotide which has an attached acceptable leaving group (X). Purine starting materials include adenine and guanine starting materials, or protected derivatives thereof. The leaving group can be attached to any carbon atom of the base of the purine, preferably at the 2-, 6-, or 8-position of the purine ring. The most preferred attachment is at the 8-position. The acceptable leaving group is displaced during the catalysis reaction and replaced by C(O)YR chemical moieties to yield the modified purine. The purine starting material can have a sugar moiety attached in the form of a ribose, deoxyribose, dideoxyribose and any combination of 2', 3' or 5' modifications thereof. The invention contemplates the above sugar moieties and any suitable derivatives thereof, such as a ribose or 2'-deoxyribose wherein the hydroxyl groups have been partially or fully protected. For example, the 5'-hydroxyl can be present as the mono-, di-, or tri-phosphate.

"Acceptable leaving group" is defined herein as a group which is a suitable counterion for palladium(II), and is designated herein as X. In the most general embodiments of this invention, X is any of a number of acceptable leaving groups well known to those skilled in the art. Acceptable leaving groups include, but are not limited to, acetate, trifluoroacetate, trifluoromethyl sulfonate, tosylate, methane sulfonate and boronic esters and acids. In the preferred embodiment, X is a halogen, and in the most preferred embodiment X is bromine or iodine. The leaving group is attached to the carbon atom of the purine starting material by methods known to one of ordinary skill in the art.

"Nucleophile" is defined herein as would be understood by one of ordinary skill in the art. Specifically, a nucleophile is an electron rich chemical moiety capable of displacing a leaving group. Due to the nature of the catalytic reaction, the CO is inserted between said nucleoside starting material and said nucleophile. Anyone skilled in the art would recognize a useful nucleophile which could be used in a nucleophilic substitution reaction. Examples of preferred nucleophiles include, but are not limited to, amines, alcohols, and thiols.

In a preferred embodiment, the general structure of the nucleophiles used in the present invention is RYH, where Y=O, S, NH, or NR'. R and R' can optionally be part of a ring-structure, which can be aromatic, aliphatic or heterocyclic. In the preferred embodiments of the invention the nucleophile (RYH) is selected from the group consisting of aliphatic or aromatic, primary or secondary amines (including cyclic amines), alcohols and thiols; wherein R and R' are selected from the group consisting of substituted or unsubstituted C1–C20 alkyl (straight-chain or branched), C2–C20 alkenyl (straight-chain or branched), aryl, heterocyclic, and natural and unnatural amino acids.

In a preferred embodiment, the nucleophile has the structure RYH, wherein,

Y is selected from the group consisting of O, S, and NH;

R is $(CH_2)_m(CH_3)_n$ wherein z is 0, 1, or 2; m is 0–19; n is 0, 1, 2, or 3; and wherein one or more of the H are optionally substituted with =O, —OH, =NH, $NH_2$, $+NMe_3Cl$,

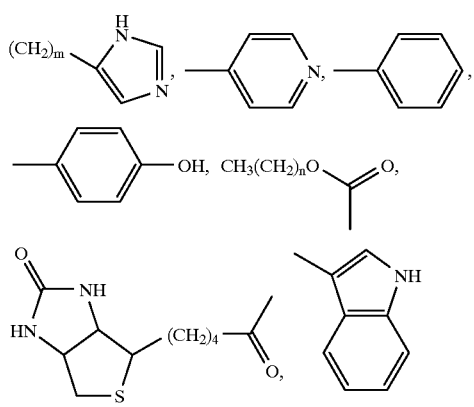

or an amino acid.

In the most preferred embodiments of the invention, the nucleophiles are selected from the following group:

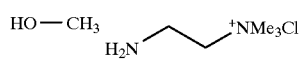

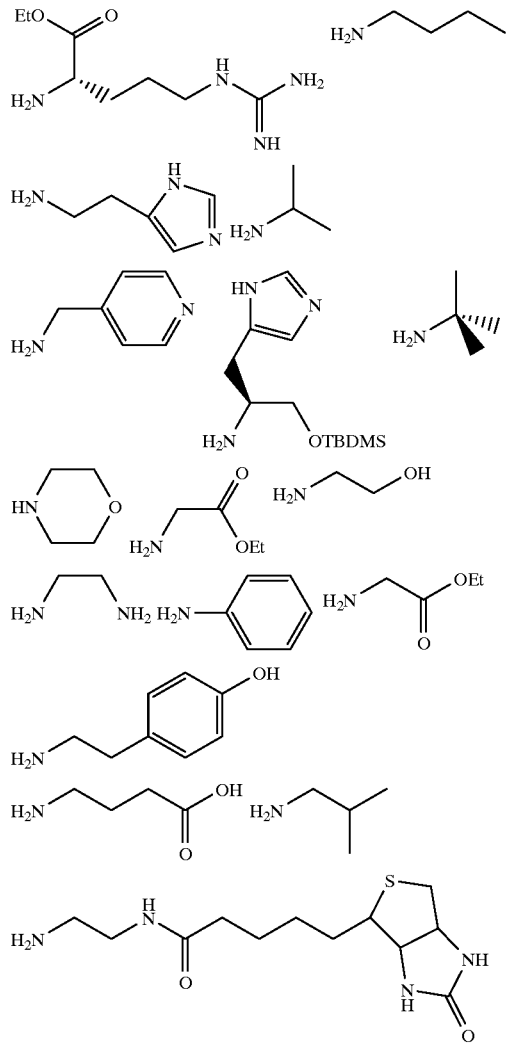

The R and R' groups of the nucleophile can include various functional groups which can be used to introduce a broad array of functional capabilities to the nucleosides prepared by this method. The nucleophile functional groups can include, among others: amides, esters, nitriles, nitros, ureas, halides, cyanates, alcohols, amines, ethers, thiols, aryl substituents, etc. as recognized by those of ordinary skill in the art. Any replacement of a hydrogen or functional group on the nucleophile is referred to as a "substitution" for the purposes of definition.

The palladium catalyst of the present invention may be characterized most generally as $PdL_4$ or $PdL_3$, where L is one of any number of commonly employed ligands of palladium. The palladium catalyst can be pre-made (e.g., $PdL_4$, wherein L is triphenyl phosphine, etc.) or made in situ from Pd(0) or Pd(II) and phosphine ligands as is known to one of ordinary skill in the art (e.g., [bis (benzylideneacetone)Pd(0)], Pd(OAc)$_2$, etc.). $PdL_4$ is the preferred palladium catalyst of the invention. It is within the skill and knowledge of those skilled in the art to recognize the various ligands that may be employed. Examples of common ligands (L) include, but are not limited to, PPh$_3$, (o-tol)$_3$P, P(p-C$_6$H$_4$SO$_3$Na)$_3$, CH$_3$CN, DMSO, N,N-dimethylformamide

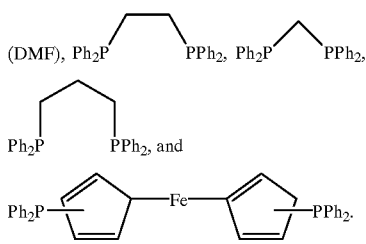

In the preferred embodiments of the catalytic species of this invention L is PPh$_3$ (triphenyl phosphine, or P(C$_6$H$_5$)$_3$) or P(p-C$_6$H$_4$SO$_3$Na)$_3$. The preparation of certain catalysts of the present invention is described in U.S. Pat. No. 5,428,149, filed Jun. 14, 1993, entitled "Method for Palladium Catalyzed Carbon-Carbon Coupling and Products" which is incorporated by reference herein.

In certain embodiments, it may be advantageous to include additional basic, non-nucleophilic components in the reaction. Examples of desirable bases include, but are not limited to, Et$_3$N, EtN(iPr)$_2$, 1,8-diazabicyclo[5.4.0]undec-7-ene (DBU), and 1,4-diazabicyclo[2.2.2]octane (DABCO). Acceptable solvents for the reaction include acetonitrile, dioxane, acetone, ethyl acetate, benzene, dimethyl formamide, dimethyl acetamide, dimethyl sulfoxide, water, THF, hexamethylphosphoramide (HMPA), and hexamethylphosphoroustriamide (HMPT). The temperature ranges for the reaction typically are between 60 and 100 degrees centigrade, however, other suitable temperature ranges are also contemplated.

The following reactant concentrations and reaction conditions are useful in the preferred embodiments of the present invention. The nucleophile is used preferably in the range from 0.0 to 2.0 M. The concentration of the palladium catalyst can range from 0.0005 to 0.2 M. The CO pressure can range from 10 to 1000 psi. The concentration of the nucleoside starting material can range from 0.010 to 1.0 M.

The modified nucleosides and nucleotides of the present invention are contemplated for use in oligonucleotides. Standard techniques for incorporation of nucleosides into oligonucleotides can be used with the modified nucleosides of the invention. Typically, the oligonucleotides of the invention are less than 500 bases, usually less than 100 bases, and most preferably less than 50 bases. The modified nucleosides are suitable for in vitro transcription procedures. The oligonucleotides containing the modified nucleosides have a number of various utilities. Specifically, the oligonucleotides interact with biological targets or have facilitating properties. The oligonucleotides can be useful in various diagnostic applications as well.

The nucleosides or nucleotides may also show antineoplastic, antibacterial, antifungal or antiviral activity. The nucleosides and nucleotides may also demonstrate other therapeutic properties. Standard assays are known to one of ordinary skill for determination of such activities. Formulation and administration routes are well known to those of ordinary skill in the art. Additionally, prodrug technology can be used as a delivery system for the nucleosides and nucleotides of the invention. Particularly, the nucleosides or nucleotides can be attached to lipids to improve pharmacology and oral availability, among other characteristics. Specifically, 5'-diacylglycero- or dialkylglycerophosphate-derivatives of the nucleosides and nucleotides of the invention are useful. These modified nucleosides and nucleotides are particularly interesting for antiviral applications. The diacylglycerophosphates of nucleosides and non-nucleosides have been used for modulation of pharmacokinetic behavior, modulation of bioavailability, and modulation of toxicity as described in U.S. Pat. No. 5,223,263 which is herein incorporated by reference.

Stability towards endo-nucleolytic degradation in serum can be achieved by introducing 2'-deoxy-2'-fluoro- or 2'-deoxy-2'-aminonucleosides to the pyrimidine positions of the ligand (Pieken et al. (1991) Science 253:314). The modified nucleosides of the present invention may also be coupled with 2' substituted species that would also be useful in a variety of situations. The incorporation of halogenated nucleosides may also prove valuable for enhanced ligand-target interaction.

EXAMPLES

The following examples are illustrative of preferred embodiments of methods of preparation and products of the invention and are not to be construed as limiting the invention thereto.

EXAMPLE 1

Purine Modifications with Amines

The following general procedures were employed to produce the modified purines of Table I.

The general scheme:

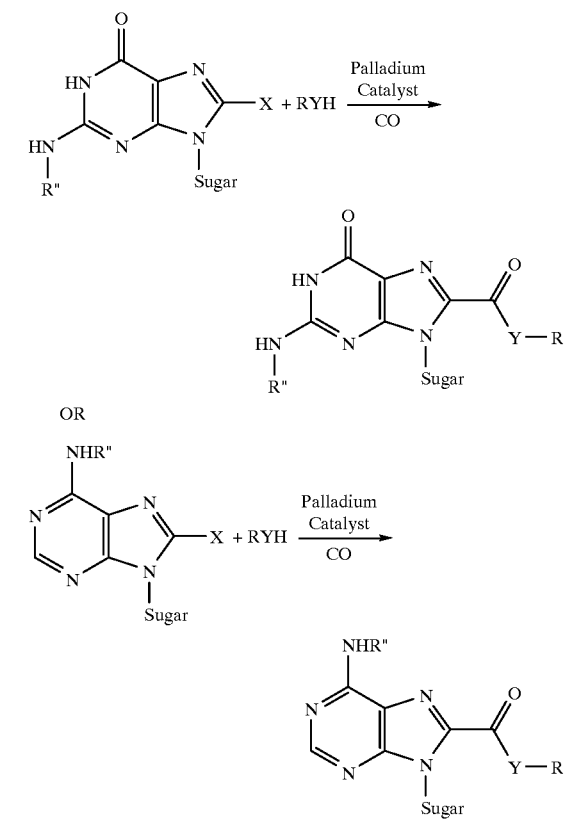

The more specific scheme:
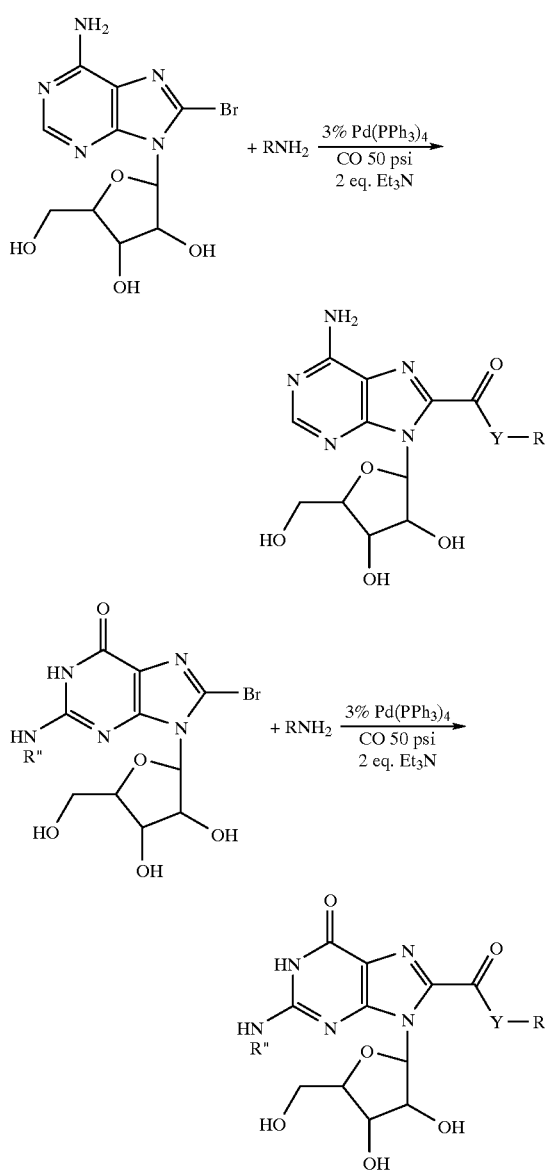
The various nucleoside base starting materials that can be used in the more specific scheme:
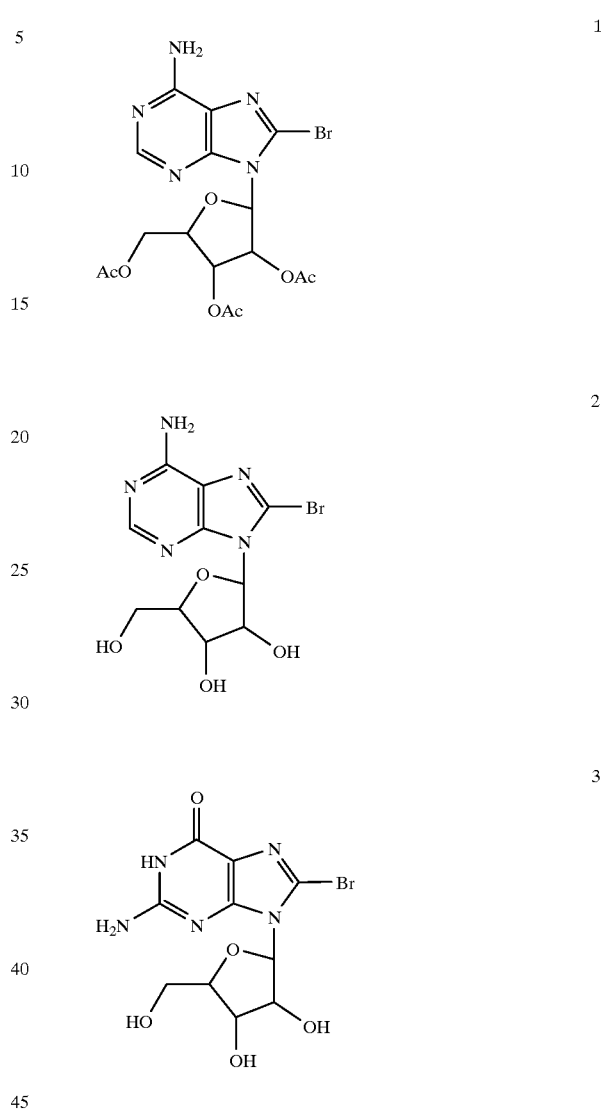
TABLE I
Examples of modified purine nucleosides.
| Entry | Nucleoside | Amine Nucleophile H₂NR | Product ID | Isolated Yield (%) |
|---|---|---|---|---|
| 1 | 1 | (morpholine) | 4 | 87[b] |
| 2 | 1 | (4-aminomethylpyridine) | 5 | 95 |

TABLE I-continued

Examples of modified purine nucleosides.

| Entry | Nucleoside | Amine Nucleophile H₂NR | Product ID | Isolated Yield (%) |
|---|---|---|---|---|
| 3 | 2 | 4-(aminomethyl)pyridine | 6 | 93 |
| 4 | 2 | H₂N-CH₂CH₂CH₂CH₃ (n-butylamine) | 7 | 84[a] |
| 5 | 2 | isopropylamine | 8 | 95 |
| 6 | 2 | tert-butylamine | 9 | 98 |
| 7 | 2 | aniline | 10 | 41 |
| 8 | 2 | H₂N-CH₂CH₂-N(Me)₃⁺Cl⁻ · HCl | 11 | 91 |
| 9 | 2 | H₂N-CH₂CH₂-OH | 12 | 62[c] |
| 10 | 2 | arginine ethyl ester | 13 | 71 |
| 11 | 3 | tert-butylamine | 14 | 85 |
| 12 | 3 | H₂N-CH₂CH₂-N(Me)₃⁺Cl⁻ · HCl | 15 | 98 |
| 13 | 3 | arginine ethyl ester | 16 | 88 |
| 14 | 3 | 4-(aminomethyl)pyridine | 17 | 81 |

TABLE I-continued

Examples of modified purine nucleosides.

| Entry | Nucleoside | Amine Nucleophile H$_2$NR | Product ID | Isolated Yield (%) |
|---|---|---|---|---|
| 15 | 3 | (structure: H$_2$N-CH$_2$CH$_2$-NH-C(O)-(CH$_2$)$_4$-biotinyl) | 18 | 56 |

[a] The reaction produced 16% of a side product with no CO insertion and direct coupling of the nucleophile to the nucleoside starting material.
[b] The reaction produced 15% of a side product with no CO insertion and direct coupling of the nucleophile to the nucleoside starting material.
[c] The reaction produced 14% of a side product with no CO insertion and direct coupling of the nucleophile to the nucleoside starting material and 14% of a product resulting from CO insertion and the hydroxide serving as nucleophile rather than the amine.

The following general procedures were followed to produce the modified purine nucleosides of Table I.

General. The $^1$H and $^{13}$C NMR spectra were obtained in CD$_3$OD, D$_2$O, CDCl$_3$, or DMSO-d$^6$ on a Bruker ARX-300 spectrometer using the deuterated solvent as an internal standard. Positive ion fast atom bombardment mass spectra (FAB$^+$) were performed at the Univ. of California at Berkeley Mass Spec. facility.

Materials. 8-Bromoadenosine, 8-bromoguanosine dihydrate, morpholine, n-butylamine, isopropylamine, tert-butylamine, aniline, 4-aminomethylpyridine, (2-aminoethyl)trimethyl-ammonium chloride, arginine ethyl ester, ethanolamine, triethylamine, DMF and N,N-dimethylacetamide (DMA) were purchased from Aldrich Chemical Company and were used as received unless otherwise noted. N-(2-Aminoethyl)biotinamide hydrobromide was purchased from Molecular Probes, Inc.

General procedure for palladium catalyzed coupling reaction. To a glass bomb with a Teflon valve was added the nucleoside specified in Table 1 (0.5 mmol), the amine nucleophile specified in Table 1 (1.0 mmol), Pd(PPh$_3$)$_4$ (0.0015 mmol), triethylamine (1.0 mmol) and DMF (or DMA). The glass bomb was evacuated and charged with CO (50 psi), then heated to the desired temperature for 24 hours. The solvent was removed and the residue was purified by flash chromatography on silica gel using a mixture of methanol in vacuo (5–30%) and methylene chloride, and/or recrystallization with methanol or isopropanol. The spectroscopic data for the coupling products follow.

Compound 4: 2',3',5'-Triacetyl-8-N-morpholine-adenosine carboxyamide $^1$H NMR (DMSO/D$_2$O) δ 2.05 (s, 3H), 2.10 (s, 3H), 2.14 (s, 3H), 3.77 (m, 2H), 3.86 (m, 6H), 4.36 (m, 2H), 4.49 (m, 1H), 5.84 (t, J=6.3 Hz, 1H), 5.92 (s, 2H), 6.12 (dd, J$_1$=6.3, J$_2$=4.0 Hz, 1H), 6.44 (d, J=4.0 Hz, 1H), 8.40 (s, 1H). $^{13}$C NMR (DMSO/D$_2$O) δ 20.5, 20.5, 20.7, 42.8, 47.9, 63.1, 66.6, 66.9, 70.4, 73.3, 79.9, 88.1, 118.3, 142.9, 150.1, 152.2, 155.1, 158.7, 169.6, 169.7, 170.6. HRMS (FAB+) m/z 507.1838 (Calc. 507.1840 for C$_{21}$H$_{26}$N$_6$O$_9$+H$^+$).

Compound 5: 2',3',5'-Triacetyl-8-N-(4-methylpyridyl)-adenosine carboxyamide $^1$H NMR (CDCl$_3$) δ 2.03 (s, 3H), 2.09 (s, 3H), 2.14 (s, 3H), 4.38 (m, 2H), 4.49 (m, 1H), 4.63 (d, J=6.2 Hz, 2H), 5.93 (s, 2H), 5.99 (t, J=6.5 Hz, 1H), 6.25 (dd, J$_1$=6.4, J$_2$=3.6 Hz, 1H), 7.28 (d, J=4.3 Hz, 2H), 7.40 (d, J=3.4 Hz, 1H), 8.15 (t, J=6.3 Hz, 1H), 8.36 (s, 1H), 8.58 (d, J=4.8 Hz, 2H). $^{13}$C NMR (CDCl$_3$) δ 20.5, 20.7, 42.1, 63.3, 70.4, 73.2, 79.6, 88.0, 118.2, 122.2, 140.3, 146.5, 150.1, 151.0, 154.5, 156.2, 158.7, 169.6, 169.8, 170.1. HRMS (FAB+) m/z 528.1842 (Calc. 528.1843 for C$_{23}$H$_{25}$N$_7$O$_8$+H$^+$).

Compound 6: 8-N-(4-pyridylmethyl)-adenosine carboxyamide $^1$H NMR (D$_2$O) d 3.72 (dd, J$_1$=12.5, J$_2$=2.3 Hz, 1H), 3.88 (dd, J$_1$=10.5, J$_2$=1.9 Hz, 1H), 4.16 (m, 1H), 4.37 (m, 1H), 4.65 (s, 2H), 4.98 (m, 1H), 7.14 (d, J=7.1 Hz, 1H), 7.43 (d, J=5.6 Hz, 2H), 8.18 (s, 1H), 8.47 (d, J=5.7 Hz, 2H). $^{13}$C NMR (DMSO/D$_2$O) δ 43.0, 64.1, 73.0, 74.7, 88.5, 91.3, 120.1, 124.0, 143.2, 150.2, 150.6, 151.5, 154.6, 158.8, 161.0. HRMS (FAB+) m/z 402.1522 (Calc. 402.1526 for C$_{17}$H$_{19}$N$_7$O$_5$+H$^+$).

Compound 7: 8-N-(n-Butyl)-adenosine carboxyamide $^1$H NMR (DMSO) δ 0.91 (t, J=7.2 Hz, 3H), 1.34 (m, 2H), 1.52 (m, 2H), 3.31 (t, J=7.2 Hz, 1H), 3.53 (m, 1H), 3.68 (m, 2H), 3.95 (d, J=2.7 Hz, 1H), 4.20 (m, 1H), 4.96 (dd, J$_1$=12.0, J$_2$=6.4 Hz, 1H), 5.13 (d, J=4.4 Hz, 1H), 5.25 (d, J=6.4 Hz, 1H), 5.59 (dd, J$_1$=8.9, J$_2$=3.4 Hz, 1H), 6.69 (d, J=6.7 Hz, 1H), 7.60 (s, 2H), 8.18 (s, 1H), 8.73 (t, J=5.8 Hz, 1H); $^{13}$C NMR (DMSO) δ 23.2, 29.1, 40.5, 48.1, 71.8, 80.4, 81.3, 95.8, 98.6, 127.4, 152.2, 159.5, 162.9, 166.4, 168.2. HRMS (FAB+) m/z 367.1723 (Calc. 367.1729 for C$_{15}$H$_{23}$N$_6$O$_5$+H$^+$).

Compound 8: 8-N-(2-Propyl)-adenosine carboxyamide $^1$H NMR (CD$_3$OD) δ 1.27 (d, J=6.5 Hz, 6H), 3.73 (dd, J$_1$=12.5, J$_2$=2.6 Hz, 1H), 3.89 (dd, J$_1$=12.5, J$_2$=2.2 Hz, 1H), 4.17 (m, 1H), 4.21 (q, J=6.5 Hz, 1H), 4.37 (dd, J$_1$=5.3, J$_2$=1.9 Hz, 1H), 4.96 (dd, J$_1$=6.9, J$_2$=4.3 Hz, 1H), 7.07 (d, J=7.2 Hz, 1H), 8.19 (s, 1H). $^{13}$C NMR (CD$_3$OD) δ 22.5, 43.1, 64.1, 72.9, 74.7, 88.4, 91.3, 119.9, 144.0, 151.4, 154.4, 158.7, 159.8. HRMS (FAB) m/z 353.1574 (Calc. 353.1573 for C$_{14}$H$_{20}$N$_6$O$_5$+H$^+$).

Compound 9: 8-N-(t-Butyl)-adenosine carboxyamide $^1$H NMR (DMSO/D$_2$O) δ 1.37 (s, 9H), 3.52 (dd, J$_1$=12.3, J$_2$=3.7 Hz, 1H), 3.66 (dd, J$_1$=12.5, J$_2$=3.1 Hz, 1H), 3.94 (m, 1H), 4.18 (m, 1H), 4.91 (t, J=5.5 Hz, 1H), 6.74 (d, J=6.8 Hz, 1H), 8.15 (s, 1H). $^{13}$C NMR (DMSO/D$_2$O) δ 28.7, 52.0, 62.7, 71.3, 72.4, 86.7, 89.5, 118.1, 143.2, 150.4, 153.9, 157.2, 158.6. HRMS (FAB+) m/z 367.1723 (Calc. 367.1717 for C$_{15}$H$_{22}$N$_6$O$_5$+H$^+$).

Compound 10: 8-N-Phenyl-adenosine carboxyamide $^1$H NMR (DMSO/D$_2$O) δ 3.74 (dd, J$_1$=12.5, J$_2$=2.6 Hz, 1H), 3.91 (dd, $J_1$=12.6, $J_2$=2.3 Hz, 1H), 4.19 (m, 1H), 4.39 (dd, $J_1$=5.4, $J_2$=2.0 Hz, 1H), 4.99 (dd, $J_1$=7.1, $J_2$=5.5 Hz, 1H), 7.18 (m, 2H), 7.39 (t, J=5.6 Hz, 2H), 7.74 (d, J=5.6 Hz, 2H), 8.21 (s, 1H). $^{13}$C NMR (DMSO) δ 62.2, 70.9, 71.9, 86.4, 89.1, 118.0, 120.0, 124.5, 128.9, 138.0, 142.7, 150.1, 153.7, 157.0, 157.3. HRMS (FAB+) m/z 387.1419 (Calc. 387.1417 for $C_{17}H_{18}N_6O_5+H^+$).

Compound 11: 8-N-(2-(N,N,N'-trimethylammonium)ethyl)-adenosine carboxyamide chloride. $^1$H NMR (CD$_3$OD) δ 3.27 (s, 9H), 3.65 (t, J=6.4 Hz, 2H), 3.73 (dd, $J_1$=12.5, $J_2$=2.5 Hz, 1H), 3.90 (m, 3H), 4.17 (m, 1H), 4.36 (dd, $J_1$=5.3, $J_2$=1.7 Hz, 1H), 4.96 (dd, $J_1$=7.1, $J_2$=5.4 Hz, 1H), 7.16 (d, J=7.2 Hz, 1H), 8.19 (s, 1H). $^{13}$C NMR (CD$_3$OD) δ 35.0, 54.1, 64.1, 65.6, 73.0, 74.6, 88.7, 91.1, 120.1, 142.7, 151.5, 154.7, 158.9, 161.1. HRMS (FAB+) m/z 396.1995 (Calc. 396.1995 for $C_{16}H_{26}N_7O_5$—Cl$^-$).

Compound 12: 8-N-(2-hydroxyethyl)-adenosine carboxyamide $^1$H NMR (DMSO/D$_2$O) δ 3.35 (m, 2H), 3.53 (m, 3H), 3.67 (dd, $J_1$=12.5, $J_2$=3.1 Hz, 1H), 3.96 (m, 1H), 4.17 (m, 1H), 4.89 (t, J=5.9 Hz, 1H), 6.86 (d, J=6.8 Hz, 1H), 8.15 (s, 1H). $^{13}$C NMR (DMSO/D$_2$O) δ 42.0, 59.8, 62.7, 71.3, 72.4, 86.7, 89.5, 118.0, 142.4, 150.5, 154.0, 157.3 159.7. HRMS (FAB) m/z 355.1372 (Calc. 355.1366 for $C_{13}H_{18}N_6O_6+H^+$).

Compound 13: 8-N-(Arginine ethyl ester)-adenosine carboxyamide $^1$H NMR (CD$_3$OD) δ 1.28 (t, J=7.1 Hz, 3H), 1.75 (m, 2H), 1.96 (m, 1H), 2.07 (m, 1H), 3.27 (m, 2H), 3.73 (dd, $J_1$=12.6, $J_2$=2.7 Hz, 1H), 3.88 (dd, $J_1$=12.6, $J_2$=2.3 Hz, 1H), 4.18 (m, 1H), 4.23 (q, J=7.1 Hz, 2H), 4.41 (dd, $J_1$=5.4, $J_2$=1.9 Hz, 1H), 4.67 (dd, $J_1$=8.9, $J_2$=5.0 Hz, 1H), 5.01 (dd, $J_1$=7.0, $J_2$=5.5 Hz, 1H), 7.09 (d, J=7.1 Hz, 1H), 8.17 (s, 1H). $^{13}$C NMR (D$_2$O/CD$_3$OD) δ 14.4, 25.6, 28.7, 41.5, 53.8, 63.1, 63.9, 72.0, 74.0, 87.5, 90.3, 119.2, 142.4, 150.4, 154.4, 157.4, 157.7, 160.1, 174.0. HRMS (FAB+) m/z (Calc. 387.1417 for $C_{17}H_{18}N_6O_5+H^+$).

Compound 14: 8-N-(t-Butyl)-guanosine carboxyamide $^1$H NMR (CD$_3$OD) δ 1.44 (s, 9H), 3.74 (dd, $J_1$=12.2, $J_2$=3.7 Hz, 1H), 3.86 (dd, $J_1$=12.2, $J_2$=2.9 Hz, 1H), 4.07 (m, 1H), 4.39 (dd, $J_1$=5.8, $J_2$=3.4 Hz, 1H), 4.95 (t, J=6.0 Hz, 1H), 6.93 (d, J=6.4 Hz, 1H). $^{13}$C NMR (DMSO/D$_2$O) δ 28.9, 52.9, 64.0, 72.4, 73.8, 87.4, 91.1, 117.5, 141.6, 154.1, 155.5, 159.7, 159.9. HRMS (FAB+) m/z 383.1676 (Calc. 383.1679 for $C_{15}H_{22}N_6O_6+H^+$).

Compound 15: 8-N-(2-(N',N',N'-trimethylammonium)ethyl) guanosine carboxyamide chloride. $^1$H NMR (D$_2$O) δ 3.24 (s, 9H), 3.64 (t, J=6.6 Hz, 2H), 3.91 (m, 4H), 4.20 (m, 1H), 4.52 (dd, $J_1$=5.1, $J_2$=3.7 Hz, 1H), 5.05 (t, J=6.0 Hz, 1H), 6.85 (d, J=6.2 Hz, 1H); $^{13}$C NMR (CD$_3$OD) δ 34.6, 54.4, 63.0, 65.0, 71.7, 73.1, 86.6, 90.1, 117.6, 140.1, 153.9, 155.1, 160.5, 161.1. HRMS (FAB+) m/z 412.1950 (Calc. 412.1945 for $C_{16}H_{26}N_7O_6$—Cl$^-$).

Compound 16: 8-N-(Arginine ethyl ester)-guanosine carboxyamide $^1$H NMR (CD$_3$OD) δ 1.28 (t, J=7.1 Hz, 3H), 1.72 (m, 2H), 1.89 (m, 1H), 2.03 (m, 1H), 3.23 (m, 2H), 3.74 (dd, $J_1$=12.1, $J_2$=3.8 Hz, 1H), 3.86 (dd, $J_1$=2.2, $J_2$=2.9 Hz, 1H), 4.06 (m, 1H), 4.21 (q, J=7.1 Hz, 2H), 4.39 (dd, $J_1$=5.7, $J_2$=2.4 Hz, 1H), 4.61 (dd, $J_1$=9.1, $J_2$=4.7 Hz, 1H), 4.98 (t, J=6.0 Hz, 1H), 6.98 (d, J=6.3 Hz, 1H). HRMS (FAB+) m/z 512.2219 (Calc. 512.2217 for $C_{19}H_{29}N_9O_8+H^+$).

Compound 17: 8-N-(4-pyridylmethyl)-guanosine carboxyamide $^1$H NMR (DMSO/D$_2$O) δ 3.51 (m, 1H), 3.64 (dd, $J_1$=11.9, $J_2$=4.4 Hz, 1H), 3.79 (m, 1H), 4.17 (dd, $J_1$=5.5, $J_2$=4.3 Hz, 1H), 4.42 (d, J=6.3 Hz, 2H), 4.91 (t, J=5.8 Hz, 1H), 6.62 (s, 2H), 6.71 (d, J=5.8 Hz, 1H), 7.29 (d, J=5.7 Hz, 2H), 8.49 (d, J=5.3 Hz, 2H), 9.45 (t, J=6.2 Hz, 1H). $^{13}$C NMR (DMSO/D$_2$O) δ 41.3, 62.2, 70.4, 71.1, 85.4, 89.0, 116.3, 122.3, 138.3, 148.4, 149.6, 152.8, 153.7, 156.7, 159.1. HRMS (FAB+) m/z 418.1482 (Calc. 418.1488 for $C_{19}H_{21}N_4O_7+H^+$).

Compound 18: 8-N-(2-Aminoethyl biotinamide)-guanosine carboxyamide $^1$H NMR (CD$_3$OD) δ 1.17 (m, 2H), 1.26 (t, J=12.0 Hz, 2H), 1.39 (m, 1H), 1.50 (m, 3H), 2.23 (t, J=12.5 Hz, 2H), 2.63 (d, J=22 Hz, 1H), 2.80 (dd, $J_1$=22, $J_2$=8.0 Hz, 1H), 2.90 (m, 1H), 3.18 (m, 2H), 3.48 (m, 4H), 3.81 (dd, $J_1$=19.5, $J_2$=6.0 Hz, 1H), 3.91 (dd, $J_1$=11.5, $J_2$=4.0 Hz, 1H), 4.08 (m, 1H), 4.19 (m, 1H), 4.40 (m, 1H), 4.47 (m, 1H), 4.96 (t, J=10 Hz, 1H), 6.83 (d, J=11 Hz, 1H). HRMS (FAB+) m/z 596.2251 (Calc. 596.2264 for $C_{23}H_{33}N_9O_8S+H^+$).

EXAMPLE 2

Purine Modification with Alcohols

The general procedure outline in Example 1 was followed to produce the modified purine described by the following scheme with the following results.

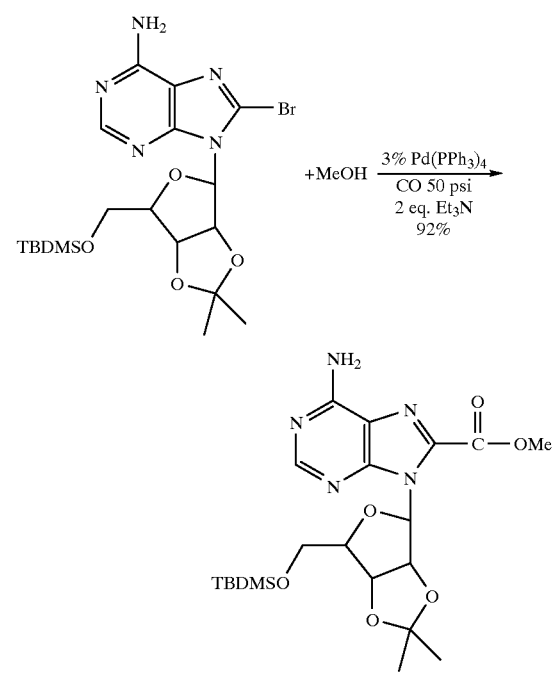

$^1$H NMR (DMSO/D$_2$O) δ −0.05 (s, 3H), −0.04 (s, 3H), 0.82 (s, 9H), 1.38 (s, 3H), 1.60 (s, 3H), 3.67 (dd, J=10.5, 6.5 Hz, 1H), 3.78 (dd, J=10.6, 6.5 Hz, 1H), 4.03 (s, 3H), 4.25 (m, 1H), 5.10 (dd, J=6.5, 3.8 Hz, 1H), 5.69 (dd, J=6.4, 2.1 Hz, 1H), 6.34 (s, 2H), 7.04 (d, J=2.2 Hz, 1H), 8.36 (s, 1H).

EXAMPLE 3

Uridine Modifications with Amines and Alcohols

The following procedures were employed to produce the modified uridine nucleosides described in Table II.

General Scheme:
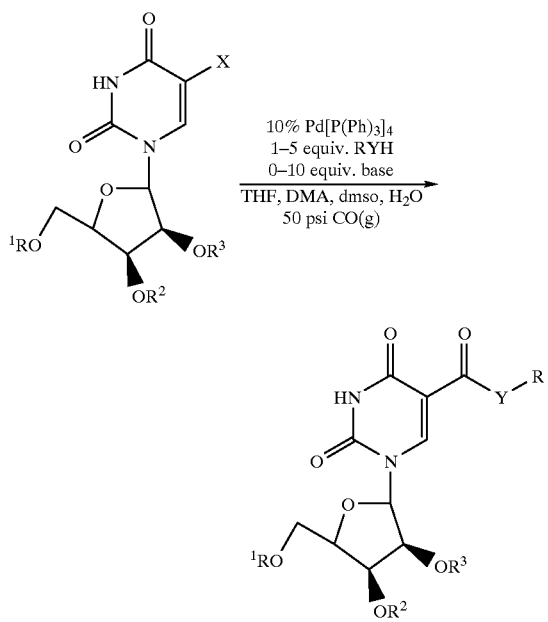
Y = O, S, NH
R = alkyl, aryl, amino acid, etc.
R$^1$ = H, DMT, TBDMS, PO$_3$Na$_2$, P$_2$O$_6$Na$_3$, P$_3$O$_9$Na$_4$
R$^2$ = R$^3$ = H, isopropylidene, Ac, SiR$_3$, etc.
X = Br, I
Specific Scheme:
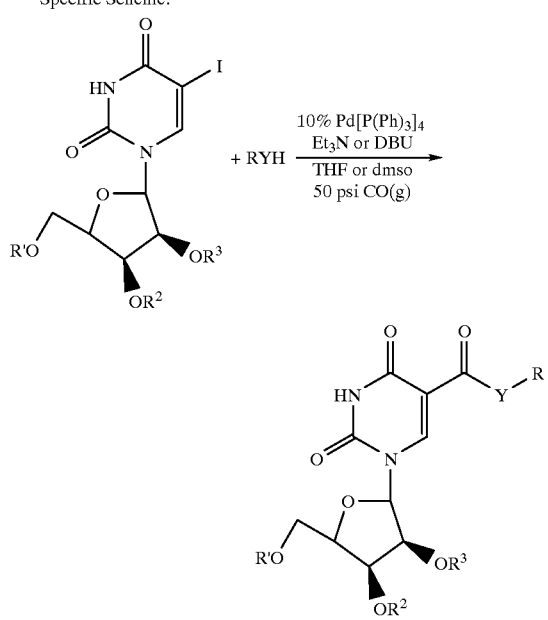
19, R$^1$ = H; R$^2$, R$^3$ = isopropylidene
20, R$^1$ = DMT; R$^2$, R$^3$ = isopropylidene
21, R$^1$ = TBDMS; R$^2$, R$^3$ = isopropylidene
22, R$^1$ = PO$_3$Na$_2$; R$^2$ = R$^3$ = H
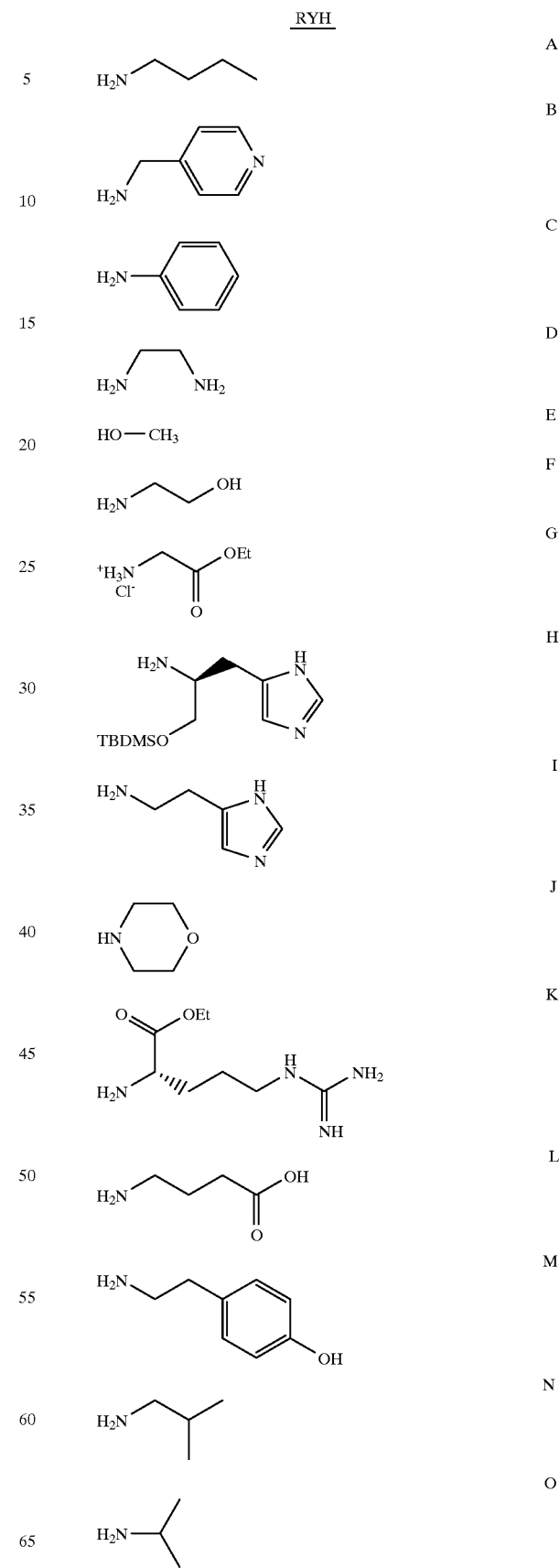

-continued

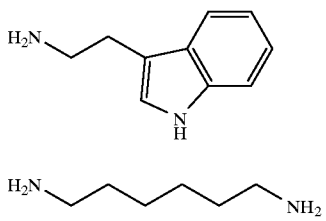
P

H₂N~~~~~NH₂
Q

TABLE II

Summary of uridine carboxyamidation products.

| Entry | Nucleoside starting material | RYH | Product ID | Isolated Yield (%) |
|---|---|---|---|---|
| 1 | 19 | A | 23 | 65 |
| 2 | 19 | B | 24 | 89 |
| 3 | 19 | C | 25 | 20 |
| 4 | 19 | D | 26 | 78 |
| 5 | 20 | E | 27 | <20 |
| 6 | 21 | E | 28 | <20 |
| 7 | 20 | H | 29 | 69 |
| 8 | 21 | I | 30 | 68 |
| 9 | 21 | F | 31 | 61 |
| 10 | 21 | G | 32 | 80 |
| 11 | 21 | J | 33 | 68 |
| 12 | 21 | K | 34 | 57 |
| 13 | 21 | P | 35 | 43 |
| 14 | 21 | Q | 36 | 62 |
| 15 | 22 | B | 37 | 90 |
| 16 | 22 | L | 38 | 74 |
| 17 | 22 | M | 39 | 66 |
| 18 | 22 | N | 40 | 96 |
| 19 | 22 | O | 41 | 90 |
| 20 | 22 | A | 42 | 86 |
| 21 | 22 | P | 43 | 34 |

Starting Material Syntheses.

Compound 22 was prepared according to a literature procedure (P. K. Chang and A. D. Welch, *J. Med. Chem.* 1963, 6, 428). The other starting materials (Compounds 19–21) were synthesized by the following procedures.

Compound 19. 5-iodo-2',3'-O-isopropylideneuridine. To a stirred solution of 5.00 g of 5-iodouridine (13.5 mmol) in 300 mL of acetone was added 250 mg of p-toluenesulfonic acid (1.30 mmol). The flask was fitted with an addition funnel filled with 4 Å molecular sieves and a reflux condenser. The solution was heated at reflux temperature for 2 h., after which all solids had dissolved. The flask was allowed to cool to room temperature and the solution concentrated in vacuo. The solution was dissolved in acetone, filtered through a plug of silica and the filtrate concentrated to give a pale yellow solid. This material was re-crystallized from ethanol to give the product as white needles in quantitative yield.

Compound 20. 5'-DMT-5-iodo-2',3'-O-isopropylideneuridine. To a stirred solution of 820 mg of 5-iodo-2',3'-isopropylideneuridine (2.00 mmol) in 1.0 mL of anhydrous DMF and 1.8 mL of anhydrous pyridine, under argon, was added 24.4 mg of 4-dimethylaminopyridine (0.20 mmol) and 745 mg of DMTCl (2.20 mmol). The solution was stirred at room temperature overnight, diluted with 150 mL of ethyl acetate, washed with 3×75 mL of H₂O, 1×50 mL of brine, and concentrated in vacuo. The residue was purified on silica gel with 40% EtOAc/hexanes to give 1.28 g (90% yield) of the product as a white solid.

Compound 21. 5'-TBDMS-5-iodo-2',3'-O-isopropylideneuridine. To a stirred solution of 1.00 g of 5-iodo-2',3'-isopropylideneuridine (2.40 mmol) in 1.9 mL of anhydrous pyridine was added 724 mg of TBDMSCl (4.80 mmol). The solution was stirred overnight at room temperature, diluted with 30 mL of ethyl acetate and washed with 3×20 mL of H₂O, 1×20 mL of brine and concentrated in vacuo. The residue was purified on silica gel with 30% EtOAc/hexanes to give 1.15 g (91% yield) of the product as a white solid.

Modified Uridine Syntheses

The modified uridines described in Table II were synthesized as follows.

Compound 23. 5-(N-Butylcarboxyamide)-2',3'-O-isopropylideneuridine. To a 300 mL stainless steel Parr bomb in an argon atmosphere glove box was added a solution of 5-iodo-2',3'-O-isopropylideneuridine (0.351 g, 1.00 mmol, in 3.0 mL of THF), 10 mL of 1.0 M Et₃N/THF (10 mmol), 3.0 mL of 1.0 M n-butylamine in THF (3.0 mmol), and tetrakis(triphenyl-phosphine)palladium (0.116 g, 0.100 mmol). The bomb was sealed, removed from the box, evacuated and charged three times with 100 psi CO, then heated at 70° C. for 24 h. The bomb was allowed to cool to room temperature, vented carefully in a fume hood, and the volatiles removed in vacuo. The crude reaction material was purified on silica gel with 5% MeOH/CH₂Cl₂ to give the product as a yellow solid (0.251 g, 65% yield). Analytical samples were obtained by crystallization from MeOH to give the product as fluffy white needles. $^1$H NMR (dmso-d₆) δ 11.92 (br s, 1H), 8.68 (t, J=5.4 Hz, 1H), 8.61 (s, 1H), 5.85 (d, J=1.8 Hz, 1H), 5.09 (t, J=4.5 Hz, 1H), 4.91 (dd, $J_1$=6.3, $J_2$=1.8 Hz, 1H), 4.74 (dd, $J_1$=6.0, $J_2$=2.7 Hz, 1H), 4.19 (m, 1H), 3.56 (m, 2H), 3.24 (m, 2H), 1.47 (s, 3H), 1.4 (m, 2H), 1.3 (m, 2H), 1.27 (s, 3H), 0.9 (t, J=7.2 Hz, 3H); $^{13}$C NMR (dmso-d₆) δ 163.3 (C4), 161.3 (CONHBu), 149.4 (C2), 146.9 (C6), 112.5 (CMe₂), 105.0 (C5), 92.8 (C1'), 87.4 (C4'), 84.4 (C2'), 80.7 (C3'), 61.2 (C5'), 38.0 (CONHCH₂—) 31.2, (NHCH₂CH₂—), 26.9 (CCH₃), 25.0 (CCH₃), 19.5 (NHCH₂CH₂CH₂CH₃), 13.6 (NHCH₂CH₂CH₂CH₃); HRMS: Calculated(observed) for C₁₇H₂₆N₃O₇: 384.1771 (384.1772). Anal. calcd.(found) for C₁₇H₂₅N₃O₇: C, 53.26(53.46); H, 6.57(6.53); N, 10.96(10.98).

Compound 24. 5-[N-(4-pyridylmethyl)carboxyamide]-2',3'-O-isopropylideneuridine. To a heavy-walled glass bomb was added 224 mg 2',3'-isopropylidene-5-iodouridine (0.542 mmol), 63 mg tetrakis(triphenylphosphine) palladium (0.0542 mmol) and anhydrous pyridine until the solids were dissolved. Pyridine was then removed in vacuo and the solids dried under high vacuum overnight. To the bomb was then added, under argon, 4 mL anhydrous THF, 0.75 mL triethylamine (5.42 mmol) and 0.22 mL 4-aminomethylpyridine (2.17 mmol). The bomb was evacuated and charged three times with CO and heated to 70° C. for 2.5 days. The bomb was allowed to cool to room temperature, the solvent removed in vacuo and the crude material loaded onto a pad of silica with dichloromethane. The pad was eluted with dichloromethane, then the desired product eluted with 10% MeOH/CH₂Cl₂ and concentrated in vacuo to a pale yellow solid. This material was purified by flash chromatography on silica gel with 5% MeOH/CH₂Cl₂ to give 201 mg (89% yield) of the product as a pale yellow solid. This material was recrystallized from methanol to give analytical samples of pure product as white needles. $^1$H NMR (dmso-d₆) δ 11.98 (s, 1H), 9.19 (t, J=6.3 Hz, 1H), 8.66 (s, 1H), 8.48 (d, 2H, J=4.5 Hz), 7.25 (d, J=5.7 Hz, 2H), 5.86 (d, J=2.2 Hz, 1H), 5.10 (t, J=4.8 Hz, 1H), 4.93 (dd, J=6.2, 2.2 Hz, 1H), 4.73 (dd, J=6.3, 3.0 Hz, 1H), 4.49 (d, J=6.3 Hz, 2H), 4.20 (m, 1H), 3.56 (t, J=4.5 Hz, 2H), 1.47 (s, 3H), 1.27 (s, 3H). $^{13}$C NMR (dmso-d$_6$) δ 163.2 (C4), 161.9 ($\underline{C}$ONH—), 149.5 (pyr o-C), 149.4 (C2), 148.4 (pyr p-C), 147.4 (C6), 122.1 (pyr m-C), 112.6 ($\underline{C}$Me$_2$), 104.8 (C5), 92.9 (C1'), 87.4 (C4'), 84.4 (C2'), 80.7 (C3'), 61.2 (C5'), 41.2 (NH $\underline{C}$H$_2$—), 26.9 (C$\underline{C}$H$_3$), 25.0 (C$\underline{C}$H$_3$); HRMS: Calculated (observed) for C$_{19}$H$_{23}$N$_4$O$_7$: 419.1567(419.1569). UV spectrum: λ$_{max}$ at 276 nm (ε=13730 M$^{-1}$cm$^{-1}$).

5-[N-(4-pyridylmethyl)carboxyamide]-5'-triphosphate-uridine. The 5'-hydroxyl compound prepared as described was converted to the 5'-triphosphate using a modified procedure of Ludwig and Eckstein, *J. Org. Chem.* 1989, 54, 631–635. After removal of the 2',3'-O-isopropylidene protecting group by stirring in H$_2$O with Dowex H$^+$ 50W×80 at 70° C., the crude triphosphate was purified successively on DEAE sephadex anion exchange resin and C18 RP-HPLC using 100 mM Et$_3$NH$^+$ HCO$_3$— and CH$_3$CN as the mobile phases. The purity of the compound was checked by analytical C18 RP-HPLC, $^1$H and $^{31}$P NMR (D$_2$O), and quantitated by its UV absorbance at 276 nm (ε=13700 M$^{-1}$cm$^{-1}$).

Compound 25. 5-(N-phenylcarboxyamide)-2',3'-O-isopropylideneuridine. To a heavy-walled glass bomb in an argon atmosphere glove box was added 2',3'-isopropylidene-5-iodouridine (0.261 g, 0.636 mmol), tetrakis(triphenylphosphine)palladium (0.083 g, 0.072 mmol), and 4.5 mL of 1.0 M Et$_3$N/THF (4.5 mmol). The bomb was sealed, removed from the box, and 0.3 mL of aniline added via syringe under argon. The flask was evacuated and charged three times with 50 psi CO and heated to 70° C. for 2 days. The bomb was cooled to room temperature, concentrated in vacuo and purified by flash chromatography on silica gel with 4–6.5% MeOH.NH$_3$/CH$_2$Cl$_2$ to give a slightly yellow solid. This material was re-crystrallized from methanol to give 52 mg (20% yield) of the pure product as fine white needles. $^1$H NMR (dmso-d$_6$) δ 12.16 (br s, 1H), 10.88 (s, 1H), 8.79 (s, 1H), 7.63 (d, J=7.8 Hz, 2H), 7.34 (m, 2H), 7.09 (t, J=7.4 Hz, 1H), 5.88 (d, J=2.1 Hz, 1H), 5.16 (t, J=4.7 Hz, 1H), 4.95 (dd, J$_1$=6.3, J$_2$=2.1 Hz, 1H), 4.76 (dd, J$_1$=6.3, J$_2$=2.7 Hz, 1H), 4.25 (m, 1H), 3.59 (m, 2H), 1.48 (s, 3H), 1.29 (s, 3H); $^{13}$C NMR (dmso-d$_6$) δ 163.6 (C4), 159.9 ($\underline{C}$ONH—), 149.3 (C2), 147.8 (C6), 138.1 (CONH$\underline{C}$<), 129.0 (phenyl m-C), 124.0 (phenyl p-C), 119.5 (phenyl o-C), 112.5 ($\underline{C}$Me$_2$), 104.6 (C5), 93.2 (C1'), 87.6 (C4'), 84.5 (C2'), 80.7 (C3'), 61.2 (C5'), 26.9 (C$\underline{C}$H$_3$), 25.0 (C$\underline{C}$H$_3$). HRMS: Calculated(observed) for C$_{19}$H$_{22}$N$_3$O$_7$: 404.1458(404.1468).

Compound 26. 5'-TBDMS-5-(N-[2-(N'-trifluoroacetamido) ethyl]-carboxyamide)-2',3'-O-isopropylideneuridine. To a heavy-walled glass bomb in an argon atmosphere glove box was added 5'-TBDMS-5-iodo-2',3'-O-isopropylideneuridine (0.531 g, 1.01 mmol), tetrakis (triphenylphosphine)palladium (0.350 g, 0.303 mmol), Et$_3$N (0.704 mL, 5.05 mmol) and 2 mL of dry THF. The bomb was sealed, removed from the box and 0.203 mL ethylenediamine (3.03 mmol) added under positive argon flow. The bomb was sealed under argon, evacuated and charged three times with 50 psi CO and heated to 70° C. overnight. The bomb was allowed to cool to room temperature, vented slowly, the solvent removed in vacuo and the crude material purified on silica gel with 25% MeOH.NH$_3$/EtOAc to give 381 mg (78% yield) of the product as a white solid. This material was protected as the N-triflouroacetamide in the following manner. To a stirred solution of 381.0 mg of the above product (0.78 mmol) in 7.0 mL of anhyd. CH$_2$Cl$_2$ at 0° C. was added dry pyridine (0.126 mL, 1.6 mmol) and (CF$_3$CO)$_2$O (0.13 mL, 0.94 mmol). The solution was stirred at 0° C. for 30 min. then 0.19 mL of (CF$_3$CO)$_2$O (1.33 mmol) and 0.13 mL of pyridine (1.7 mmol) was added. After 30 min. the reaction was allowed to warm to room temperature, concentrated in vacuo and purified by flash silica gel chromatography with 40% EtOAc/hexanes to give 174 mg (38% yield, 30% yield from iodouridine starting material) of the product as a white solid. $^1$H NMR (dmso-d$_6$) δ 11.95 (s, 1H), 9.48 (t, J=5.0 Hz, 1H), 8.81 (t, J=5.8 Hz, 1H), 8.49 (s, 1H), 5.75 (d, J=1.6 Hz, 1H), 4.89 (dd, J$_1$=6.1, J$_2$=1.7 Hz, 1H), 4.67 (dd, J$_1$=6.1, J$_2$=2.2 Hz, 1H), 4.36 (m, 1H), 3.77 (m, 2H), 3.4 (m, 2H), 3.3 (m, 2H), 1.48 (s, 3H), 1.29 (s, 3H), 0.78 (s, 9H), 0.00 (s, 3H), –0.04 (s, 3H); $^{13}$C NMR (dmso-d$_6$) δ 163.1 (C4), 162.0 ($\underline{C}$ONH—), 149.4 (C2), 147.0 (C5), 117.7, 113.9, 112.2, 104.4, 94.7, 87.8, 85.0, 81.0, 63.4, 38.1, 37.2, 26.8, 25.6, 24.9, 17.8, –5.8, –5.8. HRMS: Calculated(observed) for C$_{23}$H$_{36}$F$_3$N$_4$O$_8$Si: 581.2254(581.2249).

5'-Triphosphate-5-[N-(2-aminoethyl)carboxyamide]-uridine. The 5'-TBDMS protected ethylenediamine amide of uridine (prepared above) was desilylated with Et$_3$NH$^+$ F$^-$ in CH$_3$CN for 2 days and purified on silica gel with 20% MeOH/CH$_2$Cl$_2$ to give the 5'-hydroxyl compound, as identified by $^1$H and $^{13}$C NMR, and FAB$^+$ mass spectrometry. This compound was used for the preparation of the 5'-triphosphate using a modified of procedure of Ludwig and Eckstein, *J. Org. Chem.* 1989, 54, 631–635. After removal of the 2',3'-O-isopropylidene protecting group by stirring in H$_2$O with Dowex H$^+$ 50W×80 at 70° C., the product was purified on C18 RP-HPLC with 0.05 M TBK/CH$_3$CN as the mobile phase to give desired product in 9% yield. The product was characterized by $^1$H and $^{31}$P NMR and FAB$^+$ MS.

Compound 27. 5'-DMT-5-carbomethoxy-2',3'-O-isopropylideneuridine. In a glove box 5'-DMT-5-iodo-2',3'-O-isopropylideneuridine (1.0 mL of a solution of 0.10 g/mL, 0.14 mmol) was added to a small heavy-walled glass bomb. Solid tetrakis(triphenylphosphine)-palladium (16 mg, 0.014 mmol) was added, followed by 0.70 mmol of Et$_3$N as a 1.0 M solution in THF, and 3.0 mL of anhydrous methanol (distilled in vacuo over Mg). The bomb was evacuated and refilled with 50 psi of CO (3×), then sealed and heated to 70° C. with stirring for 3 days. The vessel was vented and the solvents removed in vacuo, and the residue dissolved in the minimum 5% MeOH/CH$_2$Cl$_2$, loaded onto a pad of silica gel, and eluted successively with CH$_2$Cl$_2$ (discarded) and 5% MeOH/CH$_2$Cl$_2$. The resultant material was purified on silica gel with 5% MeOH/CH$_2$Cl$_2$ to give the product as a colorless solid. $^1$H NMR (CD$_3$OD) δ 8.67 (s, 1H), 7.6–6.8 (m, 13H), 5.83 (d, J=2.1 Hz, 1H), 4.98 (dd, J$_1$=6.2, J$_2$=2.1 Hz, 1H), 4.59 (m, 1H), 4.32 (m, 1H), 3.76 (two s, total 6H), 3.41 (s, 3H), 3.36 (m, 2H), 1.51 (s, 3H), 1.29 (s, 3H). FAB$^+$ m/z 667 (M+Na$^+$), 645 (M+H$^+$), 303 (DMT$^+$).

Compound 28. 5'-TBDMS-5-carbomethoxy-2',3'-O-isopropylideneuridine. This compound was prepared as described above for the 5'-DMT protected compound, except using 5'-TBDMS-5-iodo-2',3'-O-isopropylideneuridine as the starting material. The product was isolated by flash chromatography on silica gel as a colorless solid. $^1$H NMR (CD$_3$OD) δ 8.58 (s, 1H), 5.71 (d, J=2.1 Hz, 1H)), 4.89 (dd, J$_1$=6.2, J$_2$=2.2, 1H), 4.75 (dd, J$_1$=6.0, J$_2$=1.8 Hz), 4.49 (m, 1H), 3.88 (m, 2H), 3.78 (s, 3H), 1.53 (s, 3H), 1.34 (s, 3H), 0.83 (s, 9H), 0.05 (s, 3H), −0.01 (s, 3H). $^{13}$C NMR (CD$_3$OD) δ 164.9 (C4), 162.2 (COOMe), 151.3 (C2), 150.3 (C6), 114.4 (CMe$_2$), 104.4 (C5), 97.3 (C1'), 90.1 (C4'), 87.4 (C2'), 83.1 (C3'), 65.1 (C5'), 52.4 (OCH$_3$), 27.4 (CCH$_3$), 26.3 (SiC[CH$_3$]$_3$), 25.3 (CCH$_3$), 19.2 (SiC[CH$_3$]$_3$), −5.4 (SiCH$_3$), −5.5 (SiCH$_3$). HRMS: Calculated(observed) mass for C$_{20}$H$_{33}$N$_2$O$_8$Si: 457.2006(457.2006).

Compound 29. 5'-TBDMS-5-(N-histidinolcarboxyamide)-2',3'-O-isopropylideneuridine. To a heavy-walled glass bomb in an argon atmosphere glove box was added 3.5 mL of a 100 mg/mL solution of 5'-TBDMS-5-iodo-2',3'-O-isopropylideneuridine (0.491 mmol), 57 mg tetrakis (triphenylphosphine)palladium (0.0491 mmol), 0.2 mL of triethylamine (1.473 mmol) and 0.5 mL of THF. The bomb was sealed, removed from the box and under argon 1.9 mL of a 100 mg/mL solution of TBDMS protected histidinol (0.736 mmol) was added. The bomb was sealed under argon, evacuated and charged three times with 50 psi CO, and heated at 70° C. for 48 h. The bomb was allowed to cool to room temperature, vented and the solvent removed in vacuo. The crude material was purified by chromatography on silica gel with either a gradient of 5–7% or 0–5% MeOH/CH$_2$Cl$_2$ to give 0.294 g (69% yield) of the desired product as a white solid. $^1$H NMR (dmso-d$_6$) δ 11.9 (br s, 2H), 8.9 (d, J=8.3 Hz, 1H), 8.6 (s, 1H), 7.5 (s, 1H), 7.3 (m, 9H), 6.8 (m, 4H), 6.7 (s, 1H), 5.9 (d, J=1.3 Hz, 1H), 5.0 (dd, J$_1$=6.3, J$_2$=1.4 Hz, 1H), 4.5 (unres. dd, 1H), 4.2 (m, 2H), 3.6 (m, 2H), 3.3 (m, 2H), 2.5 (m, 2H), 1.5 (s, 3H), 1.2 (s, 3H), 0.9 (s, 9H), 0.01 (s, 6H). $^{13}$C NMR (dmso-d$_6$) δ 163.2, 160.8, 158.0, 149.2, 148.0, 144.7, 135.3, 135.2, 134.7, 129.7, 129.5, 127.7, 127.5, 126.6, 113.1, 112.9, 105.2, 93.8, 86.4, 85.7, 83.9, 80.7, 63.9, 63.1, 54.9, 50.1, 28.5, 26.8, 25.7, 25.0, 17.9, −5.6, −5.6. HRMS: Calculated(observed) mass for C$_{46}$H$_{57}$N$_5$O$_{10}$Si: 867.3874(867.3884).

Compound 30. 5'-TBDMS-5-[N-(2-[4-imidazole]ethyl) carboxyamide]-2',3'-O-isopropylideneuridine. To a heavy-walled glass bomb in an argon atmosphere glove box was added 5'-TBDMS-5-iodo-2',3'-O-isopropylideneuridine (0.260 g, 0.496 mmol), 4 mL of dry THF, and tetrakis(triphenylphosphine)palladium (0.073 g, 0.063 mmol). The bomb was sealed, removed from the box and the solvent removed in vacuo. Under argon, anhydrous Et$_3$N (0.35 mL, 2.48 mmol), histamine (0.263 g, 2.37 mmol) and 2 mL of dmso-d$_6$ were added. The bomb was evacuated and charged three times with 50 psi CO and heated at 70° C. for 2 days. After cooling to room temperature, the bomb was vented carefully and the solvents removed in vacuo at 70° C. The crude material was purified by flash chromatography on silica gel with 12% MeOH/CH$_2$Cl$_2$ to give 181 mg (68% yield) as a slightly yellow solid. $^1$H NMR (CD$_3$OD) δ 8.6 (s, 1H), 7.6 (s, 1H), 6.9 (s, 1H), 5.7 (d, J=1.9 Hz, 1H), 4.7 (dd, J$_1$=5.9, J$_2$=1.6 Hz, 1H), 4.5 (m, 1H), 3.9 (m, 2H), 3.6 (m, 2H), 2.8 (t, 2H), 1.5 (s, 1H), 1.3 (s, 1H), 0.8 (s, 9H), 0.04 (s, 3H), −0.01 (s, 3H); $^{13}$C NMR (dmso-d$_6$) δ 163.2, 161.3, 149.4, 146.7, 134.7, 112.2, 111.8, 104.6, 94.6. 87.8, 84.9, 81.0, 63.4, 48.5, 27.0, 26.8, 25.6, 24.9, 17.9, −5.7; HRMS: Calculated(observed) for C$_{24}$H$_{37}$N$_5$O$_7$Si: 535.2462 (535.2456). UV spectrum: λ$_{max}$ at 278 nm (ε=12930 M$^{-1}$cm$^{-1}$).

5'-Triphosphate-5-[N-(2-[4-imidazole]ethyl) carboxyamide]-uridine. The 5'-TBDMS protected histamine amide of uridine (prepared above) was desilylated with Et$_3$NH$^+$F$^-$ in CH$_3$CN for 2 days and purified on silica gel with 15% NH$_3$-MeOH/CH$_2$Cl$_2$ to give the 5'-hydroxyl histamine amide of uridine, as identified by $^1$H and $^{13}$C NMR, and FAB$^+$ mass spectrometry. This compound was used for the preparation of the 5'-triphosphate using a modified procedure of Ludwig and Eckstein, *J. Org. Chem.* 1989, 54, 631–635. After removal of the 2',3'-O-isopropylidene protecting group with acidic Dowex resin in H$_2$O at 70° C., the crude triphosphate was purified successively on DEAE sephadex anion exchange resin and C18 RP-HPLC using 100 mM aq. Et$_3$NH$^+$HCO$_3^-$ and CH$_3$CN as the mobile phases. The purity of the compound was checked by analytical C18 RP-HPLC, $^1$H and $^{31}$P NMR (D$_2$O), and quantitated by its UV absorbance at 278 nm (using the ε for the nucleoside starting material, ε$_{278}$=12930 M$^{-1}$cm$^{-1}$).

Compound 31. 5'-TBDMS-5-[N-(2-hydroxyethyl) carboxyamide]-2',3'-O-isopropylideneuridine. This compound was prepared as described above for compound 30, using 3 eq. of ethanolamine and 3 eq. of triethylamine, and allowed to react for 48 h at 70° C. The product was purified on silica gel with 6% MeOH/CH$_2$Cl$_2$ to give 0.173 g (61% yield) of colorless white solid. $^1$H NMR (dmso-d$_6$) δ 11.93 (s, 1H), 8.80 (t, J=5.6 Hz, 1H), 8.48 (s, 1H), 5.75 (d, J=1.8 Hz, 1H), 4.89 (dd, J$_1$=6.1, J$_2$=1.8 Hz, 1H), 4.78 (t, J=5.1 Hz, 1H), 4.67 (unres. dd, 1H), 4.34 (m, 1H), 3.76 (d, J=3.8 Hz, 2H), 3.44 (m, 2H), 3.31 (m, 2H), 1.47 (s, 3H), 1.28 (s, 3H), 0.78 (2, 9H), −0.02 (s, 3H), −0.04 (s, 3H). $^{13}$C NMR (dmso-d$_6$) δ 163.2, 161.5, 149.4, 146.8, 112.3, 104.6, 94.5, 87.7, 84.9, 80.9, 63.4, 59.7, 41.2, 26.8, 25.6, 24.9, 17.9, −5.7, −5.8. Analytical sample from EtOAc/Hexanes. FAB$^+$ HRMS calculated(observed) for C$_{21}$H$_{36}$N$_3$O$_8$Si: 486.2272(486.2271). Anal. Calcd. (Found) for C$_{21}$H$_{35}$N$_3$O$_8$Si: C, 51.94 (52.03); H, 7.26 (7.36); N, 8.65 (8.61).

Compound 32. 5'-TBDMS-5-[N-((2-carboethoxy)ethyl) carboxyamide]-2',3'-O-isopropylideneuridine. This compound was prepared as described above for compound 30, using 1.0 eq. of glycine ethyl ester hydrochloride and 3 eq. of triethylamine. The product was purified on silica gel with 4% MeOH/CH$_2$Cl$_2$ to give 0.262 g (80% yield) of colorless white solid. $^1$H NMR (CDCl$_3$) δ 8.96 (t, J=5.5 Hz, 1H), 8.72 (s, 1H), 8.65 (s, 1H), 5.74 (d, J=2.2 Hz, 1H), 4.85 (dd, J$_1$=6.0, J$_2$=2.2 Hz, 1H), 4.72 (dd, J$_1$=6.0, J$_2$=1.6 Hz, 1H), 4.51 (m, 1H), 4.22 (q, J=7.1, 2H), 4.14 (d, J=5.6 Hz, 2H), 3.96 (m, 1H), 3.78 (m, 1H), 1.58 (s, 3H), 1.36 (s, 3H), 1.28 (t, J=7.1 Hz, 3H), 0.82 (s, 9H), 0.04 (s, 3H), −0.01 (s, 3H). $^{13}$C NMR (CDCl$_3$) δ 169.6, 163.1, 161.8, 149.4, 147.3, 112.3, 104.1, 94.6, 87.8, 84.9, 81.0, 63.4, 60.4, 40.8, 26.9, 25.6, 24.9, 17.9, 14.0, −5.8. Analytical sample from EtOAc/Hexanes. FAB$^+$ HRMS calculated (observed) for C$_{23}$H$_{38}$N$_3$O$_9$Si: 528.2377(528.2382). Anal. Calcd. (Found) for C$_{23}$H$_{37}$N$_3$O$_9$Si: C, 52.36 (52.19); H, 7.07 (6.93); N, 7.96 (7.85).

Compound 33. 5'-TBDMS-5-[morpholinecarboxyamide]-2',3'-O-isopropylideneuridine. This compound was prepared as described above for compound 30, using 3 eq. of morpholine and 3 eq. of triethylamine. The product was purified on silica gel with 4% MeOH/CH$_2$Cl$_2$ 0.202 g (68% yield) of colorless white solid. $^1$H NMR (dmso-d$_6$) δ 11.65 (s, 1H), 7.90 (s, 1H), 5.80 (d, J=2.2 Hz, 1H), 4.93 (dd, J=6.2, 2.2 Hz, 1H), 4.68 (6.2, 3.4 Hz, 1H), 4.12 (m, 1H), 3.76 (m, 2H), 3.5 (br m, 6H), 3.29 (br m, 2H), 1.47 (s, 3H), 1.28 (s, 3H), 0.84 (s, 9H), 0.03 (s, 6H). $^{13}$C NMR (dmso-d$_6$) δ 162.3, 160.3, 149.7, 142.2, 112.9, 111.1, 66.2, 65.9, 63.0, 47.0, 41.9, 26.9, 25.8, 25.1, 18.0, −5.5, −5.6. Analytical sample from EtOAc/Hexanes. FAB$^+$ HRMS calculated(observed) for C$_{23}$H$_{38}$N$_3$O$_8$Si: 512.2428(512.2436).

Compound 34. 5'-TBDMS-5-[N-(arginine ethyl ester) carboxyamide]-2',3'-O-isopropylideneuridine. To a heavy-walled glass bomb in an argon atmosphere glove box was added 5'-TBDMS-5-iodo-2',3'-O-isopropylideneuridine (0.238 g, 0.453 mmol), arginine ethyl ester dihydrochloride (0.260 g, 0.94 mmol), tetrakis (triphenylphosphine)-palladium (0.052 g, 0.045 mmol), $Et_3N$ (0.32 mL, 2.3 mmol), 3 mL of dry THF, and 2 mL of DMSO. The reaction vessel was evacuated and charged with 50 psi of CO three times, then heated to 70° C. for 2 days. The crude mixture was concentrated and chromatographed on silica gel with 25% MeOH—$NH_3$/EtOAc to give the product as an off-white solid, 0.160 g (57% yield). $^1$H NMR ($CD_3OD$) δ 8.55 (s, 1H), 5.64 (d, J=1.9 Hz, 1H), 4.77 (unres. dd, 1H), 4.68 (unres dd, 1H), 4.22 (q, J=7.1 Hz, 2H), 4.17 (m, 1H), 3.93 (m, 1H), 3.75 (m, 2H), 3.43 (br m, 2H), 2.0 (br m, 1H), 1.78 (br m, 3H), 1.50 (s, 3H), 1.34 (s, 3H), 1.26 (t, J=7.1 Hz, 3H), 0.92 (s, 9H), 0.13 (s, 6H).

Compound 35. 5-[N-(2-[3-indolyl]ethyl)carboxyamide)-2',3'-O-isopropylideneuridine. To a heavy-walled glass bomb in an argon atmosphere glove box was added 5'-TBDMS-5-iodo-2',3'-O-isopropylideneuridine (1.13 g, 2.14 mmol), 2-(3-indolyl)ethylamine (1.70 g, 10.7 mmol) and tetrakis(triphenylphosphine)palladium (0.247 g, 0.214 mmol), anhydrous triethylamine (1.5 mL, 10.7 mmol), and 10 mL of THF. The bomb was sealed, and evacuated and charged three times with 50 psi CO, then heated at 70° C. for 16 h. After cooling, and removal of the solvents in vacuo, the crude material was purified on silica gel with 0–5% MeOH/$CH_2Cl_2$ to give 0.895 g of slightly impure yellow solid (78% crude yield). Desylation was accomplished by stirring the above material in 2 mL of anhyd. $CH_3CN$ with $Et_3N·HF$ (1.0 g, 8.4 mmol) for 16 h at ambient temp. The reaction mixture was diluted with 30 mL of EtOAc and extracted with 3×20 mL of $H_2O$, 10 mL of brine, then concentrated in vacuo and purified on silica gel with 0–5% MeOH/$CH_2Cl_2$ to give the desired product as a pale yellow solid (0.430 g, 43% yield). $^1$H MNR ($CD_3OD$) δ 10.2 (br s, 1H), 9.1 (t, 1H), 8.7 (s, 1H), 7.5 (d, J=7.8 Hz, 1H), 7.3 (d, J=8.1 Hz, 1H), 7.0 (m, 3H), 5.9 (d, J=2.1 Hz, 1H), 4.3 (t, 1H), 3.7 (m, 4H), 3.0 (t, 2H), 1.5 (s, 1H), 1.3 (s, 1H).

5'-Triphosphate-5-[N-(2-[3-indolyl]ethyl)carboxyamide) uridine. The 5'-TBDMS protected tryptamine amide of uridine (prepared above) was desilylated with 5 eq. of $Et_3NH^+F^-$ in $CH_3CN$ for 18 h at RT and purified on silica gel to give the 5'-hydroxyl compound in 43% yield, as identified by $^1$H and $^{13}$C NMR, and FAB$^+$ mass spectrometry. The 5'-hydroxyl compound was then used for the preparation of the 5'-triphosphate using a modified of procedure of Ludwig and Eckstein, *J. Org. Chem.* 1989, 54, 631–635. After removal of the 2',3'-O-isopropylidene protecting group by stirring in $H_2O$ with Dowex H$^+$ 50W×80 at 70° C., the product was purified on DEAE sephadex with 0.05–1.5 M TBK buffer with 25% added $CH_3CN$, followed by C18 RP-HPLC with 0.05 M TBK/$CH_3CN$ mobile phase as eluant. The triphosphate was characterized by $^1$H and $^{31}$P NMR and FAB$^+$ MS.

Compound 36. 5'-TBDMS-5-(N-[6-aminohexyl]-carboxyamide)-2',3'-O-isopropylideneuridine. To a heavy-walled glass bomb in an argon atmosphere glove box was added 5'-TBDMS-5-iodo-2',3'-O-isopropylideneuridine (1.28 g, 2.40 mmol), 1,6-diaminohexane (1.40 g, 12.0 mmol) and tetrakis (triphenylphosphine)palladium (0.83 g, 0.72 mmol) and 10 mL of THF. The bomb was sealed, removed from the box and triethylamine (1.7 mL, 12.0 mmol) was added under argon via syringe. The vessel was evacuated and charged three times with 50 psi CO and heated at 70° C. overnight. The bomb was allowed to cool, vented, and the solvent removed in vacuo. The crude material was dissolved in 10 mL of methanol and the palladium catalyst removed by filtration. The filtrate was concentrated and purified on silica gel with 15–25% $NH_3$—$CH_3OH$ in $CH_2Cl_2$ to give the desired product (0.812 g, 62% yield) as a white solid. $^1$H NMR ($CD_3OD$) δ 9.0 (s, 1H), 5.7 (d, J=1.8 Hz, 1H), 4.9 (m, 1H), 4.7 (m, 1H), 4.5 (br s, 1H), 3.9 (m, 2H), 3.3 (m, 3H), 2.9 (t, 2H), 1.5 (unres. m, 12H), 0.8 (s, 9H), 0.04 (s, 3H), 0.0 (s, 3H).

5-(N-[6-N'-trifluoroacetamidohexyl]-carboxyamide)-2',3'-O-isopropylideneuridine. The free amine of the above compound was protected in the following manner. To a stirred solution of compound 36 in acetonitrile with catalytic triethylamine was added 2.0 eq. ethyl triflouroacetate. The solution was stirred at RT for 18 h, and an additional 1.6 eq. ethyl triflouroacetate added and the solution stirred for 20 h. Concentration and purification on silica gel with 1–5% MeOH/$CH_2Cl_2$ gave the desired triflouroacetamide in 25% yield, as characterized by $^1$H NMR. The compound was then desilylated with 5 eq. of $Et_3NH^+F^-$ in $CH_3CN$ for 18 h at RT and purified on silica gel to give the 5'-hydroxyl compound in quantitative yield, as identified by its $^1$H NMR spectrum.

General prodedure for compounds 37–43. To a glass pressure reactor equipped with a Teflon valve were added nucleotide (0.1 mmol), the amine (0.5 mmol, 5 eq.), Pd(PPh$_3$)$_4$ (0.01 mmol, 0.1 eq.), and dimethyl sulfoxide as solvent (0.5 mL). The reactor was evacuated and charged with CO (50 psi) three times before heating to 60° C. for 24 hours. The crude mixture was purified on a DEAE Sephadex A-25 anion exchange column using a linear gradient of 0.05 M to 1.0 M triethylammonium bicarbonate buffer. Characterization of the compounds follows.

Compound 37. $^1$H NMR ($D_2O$) δ 4.0 (m, 2H), 4.23 (m, 1H), 4.28 (t, J=4.5 Hz, 1H), 4.43 (t, J=5.2 Hz, 1H), 4.60 (s, 2H), 5.93 (d, J=5.1 Hz, 1H), 7.34 (d, J=4.8 Hz, 2H), 8.42 (d, J=4.8 Hz, 2H), 8.55 (s, 1H). $^{13}$C NMR ($CD_3OD$) δ 43.2, 64.9, 71.1, 74.9, 85.1, 90.7, 106.9, 123.4, 147.7, 149.4, 150.2, 152.1, 165.0, 165.5. $^{31}$P NMR ($CD_3OD$) δ 6.4. HRMS (FAB+) m/z 459.0909 (Calc. 459.0917 for $C_{16}H_{19}N_4O_{10}P+H^+$).

Compound 38. $^1$H NMR ($D_2O$) δ 1.79 (m, 2H), 2.20 (t, J=7.5 Hz, 2H), 3.34 (t, J=6.9 Hz, 2H), 4.08 (m, 2H), 4.28 (m, 2H), 4.37 (t, J=4.8 Hz, 1H), 5.92 (d, J=4.9 Hz, 1H), 8.55 (s, 1H). $^{13}$C NMR ($D_2O$) δ 26.8, 36.0, 39.9, 65.0, 71.3, 74.6, 84.4, 90.6, 107.2, 146.2, 159.3, 167.1, 174.4, 183.6. $^{31}$P NMR ($CD_3OD$) δ 8.2. MS (FAB) m/z 454.0858 (Calc. 454.0863 for $C_{14}H_{20}N_3O_{12}P+H^+$).

Compound 39. $^1$H NMR ($D_2O$) δ 2.73 (t, J=6.7 Hz, 2H), 3.50 (t, J=6.7 Hz, 2H), 4.03 (m, 2H), 4.25 (m, 2H), 4.36 (t, J=4.8 Hz, 1H), 5.87 (d, J=4.9 Hz, 1H), 6.76 (d, J=8.3 Hz, 2H), 7.08 (d, J=8.3 Hz, 2H), 8.44 (s, 1H). $^{13}$C NMR ($CD_3OD$) δ 34.6, 41.9, 65.0, 71.0, 74.9, 8439, 90.7, 106.9, 116.4, 131.2, 131.9, 147.2, 151.8, 155.0, 164.6, 164.7. $^{31}$P NMR ($CD_3OD$) δ 8.1. HRMS (FAB+) m/z 488.1082 (Calc. 488.1084 for $C_{18}H_{22}N_3O_{11}P+H^+$).

Compound 40. $^1$H NMR ($D_2O$) δ 0.87 (d, J=6.7 Hz, 6H), 1.82 (m, 1H), 4.03 (m, 2H), 4.27 (m, 2H), 4.39 (t, J=5.0 Hz, 1H), 5.91 (d, J=5.1 Hz, 1H), 8.53 (s, 1H). $^{13}$C NMR (MeOD) δ 20.3, 29.0, 43.3, 65.1, 71.0, 75.0, 85.0, 90.6, 107.2, 147.3, 151.9, 164.8, 165.0. $^{31}$P NMR ($CD_3OD$) δ 6.4. HRMS (FAB+) m/z 424.1129 (Calc. 424.1121 for $C_{14}H_{22}N_3O_{10}P+H^+$).

Compound 41. $^1$H NMR ($D_2O$) δ 1.16 (d, J=5.4 Hz, 6H), 4.02 (m, 3H), 4.28 (m, 2H), 4.38 (t, J=5.0 Hz, 1H), 5.90

(d, J=3.6 Hz, 1H), 8.50 (s, 1H). $^{13}$C NMR (D$_2$O) δ 164.9, 163.7, 151.9, 147.1, 107.2, 90.6, 85.0, 75.0, 71.0, 65.1, 43.0, 22.5. $^{31}$P NMR (D$_2$O) δ 6.5.

Compound 42. $^1$H NMR (D$_2$O) δ 0.86 (t, J=7.3 Hz, 3H), 1.32 (m, 2H), 1.51 (m, 2H), 3.31 (m, 2H), 3.99 (m, 2H), 4.23 (m, 1H), 4.28 (m, 1H), 4.40 (t, J=5.1 Hz, 1H), 5.91 (d, J=5.1 Hz, 1H), 8.50 (s, 1H). $^{13}$C NMR (1:1 D$_2$O:CD$_3$OD) δ 14.0, 20.7, 31.8, 40.0, 65.0, 71.4, 75.0, 85.3, 90.5, 107.0, 147.2, 152.8, 164.8, 166.1. $^{31}$P NMR (D$_2$O) δ 7.7. HRMS (FAB+) m/z 424.1121 (Calc. 424.1121 for C$_{14}$H$_{22}$N$_3$O$_{10}$P+H$^+$).

Compound 43. H NMR (D$_2$O) δ 2.88 (t, J=6.3 Hz, 2H), 3.53 (t, J=6.3 Hz, 2H), 3.96 (s, 2H), 4.20 (d, J=2.3 Hz, 2H), 4.30 (t, J=4.0 Hz, 1H), 5.78 (d, J=4.7 Hz, 1H), 6.97 (t, J=7.5 Hz, 1H), 7.08 (m, 2H), 7.34 (d, J=8.0 Hz, 1H), 7.46 (d, J=7.8 Hz, 1H), 8.22 (s, 1H). $^{13}$C NMR (D$_2$O) δ 25.0, 40.1, 64.8, 71.1, 74.7, 84.8, 90.8, 106.8, 112.7, 119.5, 120.0, 122.8, 124.5, 127.8, 137.2, 146.6, 152.7, 164.8, 165.9. $^{31}$P NMR (MeOD) δ 8.2. HRMS (FAB+) m/z 511.1236 (Calc. 511.1230 for C$_{20}$H$_{23}$N$_4$O$_{10}$P+H$^+$).

EXAMPLE 4

Cytidine Modifications with Amines

The following procedures were employed to produce the modified cytidines shown in Table III.

General Scheme:

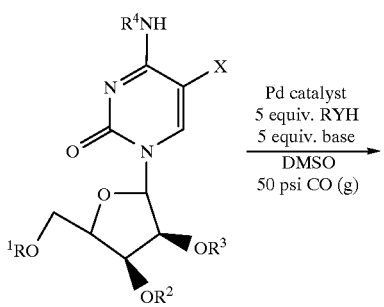

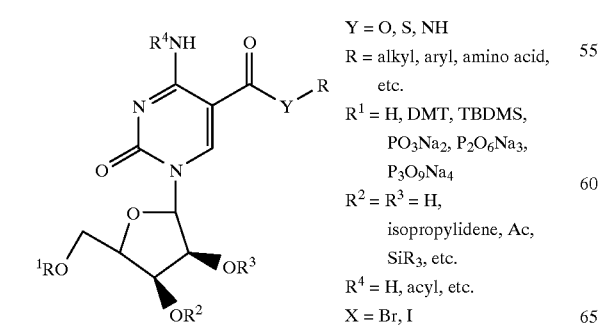

Y = O, S, NH
R = alkyl, aryl, amino acid, etc.
R$^1$ = H, DMT, TBDMS, PO$_3$Na$_2$, P$_2$O$_6$Na$_3$, P$_3$O$_9$Na$_4$
R$^2$ = R$^3$ = H, isopropylidene, Ac, SiR$_3$, etc.
R$^4$ = H, acyl, etc.
X = Br, I Specific Scheme:

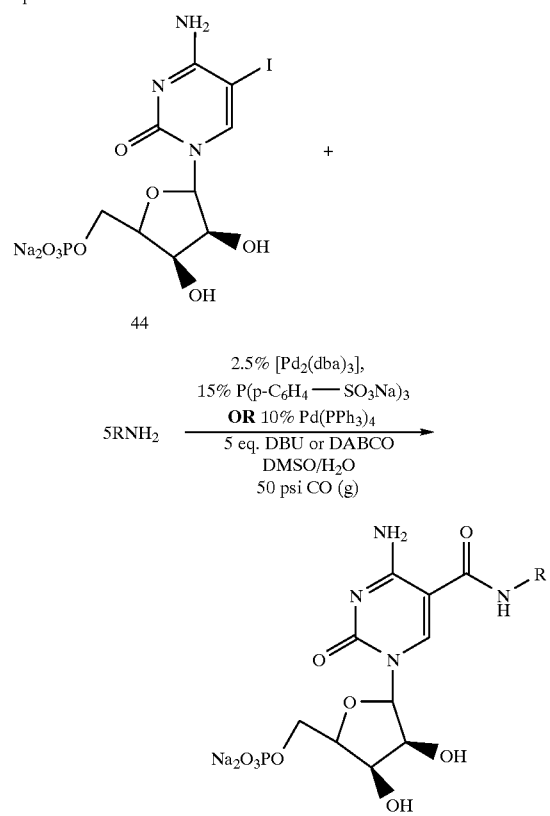

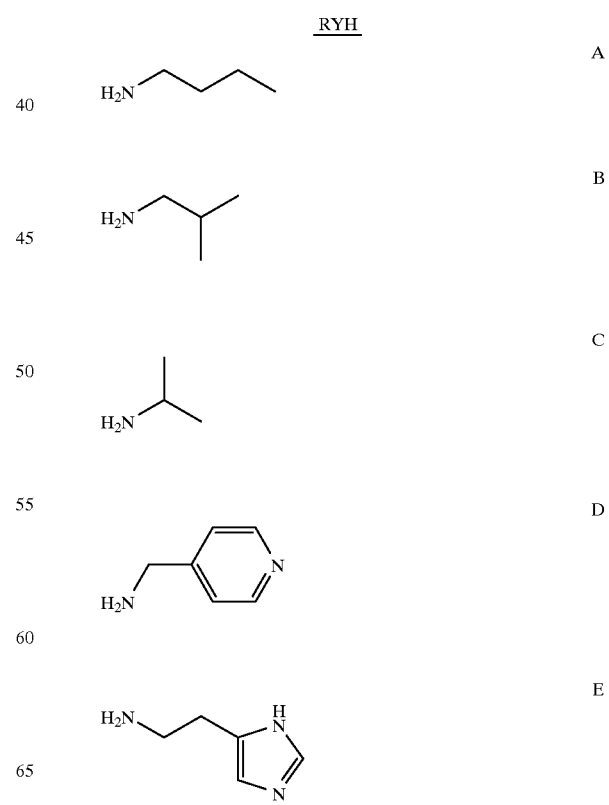

-continued

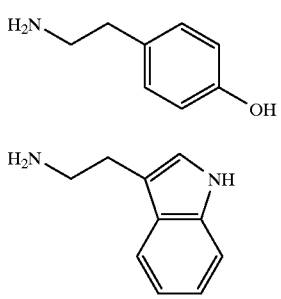

F

G

TABLE III

Summary of cytidine carboxyamidation products.

| Entry | Starting material | RNH$_2$ | Product ID | Isolated Yield (%) |
|---|---|---|---|---|
| 1[a] | 44 | A | 45 | 73 |
| 2[b] | 44 | B | 46 | 42 |
| 3[a] | 44 | C | 47 | 80 |
| 4[c] | 44 | D | 48 | 36 |
| 5[c] | 44 | E | 49 | 20 |
| 6[b] | 44 | F | 50 | 49 |
| 6[c] | 44 | G | 51 | 81 |

[a]Nucleotide (0.1 mmol), RNH$_2$ (0.5 mmol), Pd(PPh$_3$)$_4$ (0.01 mmol), DBU (0.5 mmool), DMSO (0.5 mL).
[b]Nucleotide (0.1 mmol), RNH$_2$ (0.5 mmol), Pd$_2$(dba)$_3$ (2.5 μmol), P(p-C$_6$H$_4$—SO$_3$Na)$_3$ (0.015 mmol), DABCO (0.7 mmol), DMSO (0.5 mL).
[c]Nucleotide (0.1 mmol), RNH$_2$ (0.5 mmol), Pd(PPh$_3$)$_4$ (0.01 mmol), DBU or DABCO (0.5 mmol), DMSO:H$_2$O 93:7 (0.5 mL).

General Information

5-Iodocytidine monophosphate was synthesized according to a literature procedure (Voytek, P.; Chang, P. K.; Prusoff, W. H. J. Biol. Chem. 1971, 246, 1432). Trisulfonated triphenylphosphine sodium salt was purchased from Strem Chemicals, Inc. All other compounds were purchased from Aldrich Chemical Co. n-Butylamine, isopropylamine, triethylamine, and 1,8-diazabicyclo(5.4.0)undec-7-ene (DBU) were purchased from Aldrich Chemical Co. and distilled from CaH$_2$. Isobutylamine, tyramine hydrochloride, and 4-aminobutyric acid (Acros Organics) were used as is. Histamine was purchased from Sigma Chemical Co. and used as is. Cytidine monophosphate, Pd$_2$(dba)$_3$, tetrakis(triphenylphosphine)palladium(0), DABCO, 4-aminomethylpyridine, and DMSO were purchased from Aldrich Chemical Co. and used as is. The $^1$H and $^{13}$C NMR spectra were obtained in CD$_3$OD, D$_2$O, or DMSO-d$^6$ using a Bruker ARX-300 spectrometer and referenced to solvent resonances. High resolution fast atom bomdardment mass spectra (HR FAB MS) were obtained using VG 70 SE & ZAB2-EQ/FAB(+).

General procedure

The general procedure to synthesize the compounds of Table III is provided. To a heavy-walled glass pressure reactor equipped with a Teflon valve were added nucleotide (0.1 mmol), amine (0.5 mmol), Pd(PPh$_3$)$_4$ (0.01 mmol), DBU (0.5 mmol), DMSO (0.5 ml). The reactor was evacuated and charged with CO (50 psi) three times before heating to 60° C. for 24 hours. The crude mixture was quantitatively analyzed by reverse phase HPLC. The products were purified on a DEAE Sephadex A-25 ion exchange column using a linear gradient (0.05 M to 1.0 M) of triethylammonium bicarbonate followed by preparative C-18 reverse phase HPLC (0.05 M thiethylammonium hydrogen carbonate/MeOH). Characterization of the compounds listed in Table III follows.

Compound 45. 5-(N-Butylcarboxyamide)-cytidine monophosphate. $^1$H NMR (CD$_3$OD) δ 0.85 (t, J=7.4 Hz, 3H), 1.29 (m, 2H), 1.49 (m, 2H), 3.24 (m, 2H), 4.05 (m, 2H), 4.25 (m, 2H), 4.33 (m, 1H), 5.87 (d, J=4.1 Hz, 1H), 8.38 (s, 1H). $^{13}$C NMR (CD$_3$OD) δ 14.2, 20.7, 31.7, 40.7, 64.6, 70.8, 75.6, 84.9. 91.1, 102.8, 144.3, 157.3, 164.8, 167.0. $^{31}$P NMR (CD$_3$OD) δ 5.8. HRMS (FAB+) m/z 423.1275 (Calc. 423.1281 for C$_{14}$H$_{23}$N$_4$O$_9$P+H$^+$).

Compound 46. 5-(N-Isobutylcarboxyamide)-cytidine monophosphate. $^1$H NMR (CD$_3$OD) δ 0.92 (d, J=3.0 Hz, 3H), 0.94 (d, J=3.0 Hz, 3H), 1.99 (m, 1H), 3.12 (m, 2H, overlapped with Et$_3$NH$^+$), 4.07 (m, 1H), 4.16 (m, 2H), 4.29 (m, 2H), 5.99 (d, J=4.9 Hz, 1H), 8.66 (s, 1H). $^{13}$C NMR (60:1 D$_2$O:CD$_3$OD) δ 20.6, 20.6, 29.0, 48.2, 64.8, 70.7, 75.5, 84.6, 91.4, 103.0, 144.3, 157.3, 164.8, 167.3.

Compound 47. 5-(N-Isopropylcarboxyamide)-cytidine monophosphate. $^1$H NMR (CD$_3$OD) δ 1.22 (m, 6H), 4.06 (m, 3H), 4.24 (m, 1H), 4.28 (m, J=4.9 Hz, 1H), 4.38 (t, J=5.0 Hz, 1H), 5.89 (d, J=4.8 Hz, 1H), 8.31 (s, 1H). $^{13}$C NMR (CD$_3$OD) δ 22.3, 43.5, 64.9, 70.8, 75.1, 84.8, 91.2, 103.3, 144.6, 157.4, 164.7, 166.5. $^{31}$P NMR (CD$_3$OD) δ 5.6. HRMS (FAB+) m/z 409.1119 (Calc. 409.1124 for C$_{13}$H$_{21}$N$_4$O$_9$P+H$^+$).

Compound 48. 5-[N-(4-pyridylmethyl)carboxyamide] cytidine monophosphate. $^1$H NMR (DMSO-d$_6$) δ 2.99 (q, J=7.3 Hz, 6H), 3.88 (m, 1H), 3.98 (m, 2H), 4.03 (m, 1H), 4.13 (m, 1H), 4.32 (d, J=5.2 Hz, 2H), 5.92 (d, J=5.7 Hz, 1H), 7.32 (d, J=5.4 Hz, 2H), 7.80 (s, 1H), 8.44 (d, J=4.8 Hz, 2H), 8.50 (m, 1H), 8.79 (s, 1H), 10.38 (m, 1H). $^{13}$C NMR (DMSO-d$_6$) δ 41.8, 63.9, 70.4, 74.5, 83.7, 88.4, 98.6, 122.4, 144.0, 149.0, 149.2, 153.9, 162.3, 163.7, 165.2. $^{31}$P NMR (CD$_3$OD) δ 6.5. HRMS (FAB+) m/z 458.1082 (Calc. 458.1077 for C$_{16}$H$_{20}$N$_5$O$_9$P+H$^+$).

Compound 49. 5-[N-(2-[4-imidazole]ethyl)carboxyamide] cytidine monophosphate. $^1$H NMR (1:1 D$_2$O:CD$_3$OD) δ 3.06 (m, 2H), 3.60 (m, 1H), 3.68 (m, 1H), 4.12 (m, 2H), 4.25 (m, 1H), 4.29 (m, 2H), 5.95 (d, J=3.8 Hz, 1H), 7.27 (s, 1H), 8.50 (s, 1H), 8.53 (s, 1H). $^{13}$C NMR (1:1 D$_2$O:CD$_3$OD) δ 27.9, 67.5, 73.8, 79.1, 88.0, 93.7, 104.7, 120.2, 135.9, 136.8, 147.3, 159.3, 167.8, 170.1. $^{31}$P (1:5 CD$_3$OD:DMSO-d$_6$) δ 6.5. HRMS (FAB+) m/z 461.1186 (Calc. 461.1186 for C$_{15}$H$_{21}$N$_6$O$_9$P+H$^+$).

Compound 50. 5-[N-(2-[4-hydroxyphenyl]ethyl) carboxyamide]cytidine monophosphate. $^1$H NMR (D$_2$O) δ 2.82 (t, J=6.8 Hz, 2H), 3.52 (m, 2H), 3.97 (m, 1H), 4.02 (m, 1H), 4.28 (m, 2H), 4.33 (t, J=4.6 Hz, 1H), 5.88 (d, J=4.5 Hz, 1H), 6.83 (d, J=8.4 Hz, 2H), 7.17 (d, J=8.4 Hz, 2H), 8.24 (s, 1H). $^{13}$C NMR (D$_2$O) δ 34.8, 42.0, 64.4, 70.9, 75.7, 85.0, 91.1, 102.7, 116.2, 131.3, 132.3, 144.2, 155.1, 157.2, 164.7, 166.9. $^{31}$P NMR (D$_2$O) 7.8.

Compound 51. 5-[N-(2-indolylethyl)carboxyamide]cytidine monophosphate. $^1$H NMR (CD$_3$OD) δ 2.94 (m, 2H), 3.55 (m, 2H), 4.04 (m, 1H), 4.11 (m, 2H), 4.20 (m, 2H), 5.92 (d, J=4.2 Hz, 1H), 6.91 (m, 1H), 6.99 (m, 1H), 7.06 (s, 1H), 7.25 (d, J=4.1 Hz, 1H), 7.61 (d, J=7.5 Hz, 1H), 8.56 (s, 1H). MS (FAB−) m/z (M−H)$^-$ 507.7.

EXAMPLE 5

2'-Deoxycytidine Modifications with Amines

The following procedures were employed to produce the modified 2'-deoxycytidines shown in Table IV.

General Scheme:

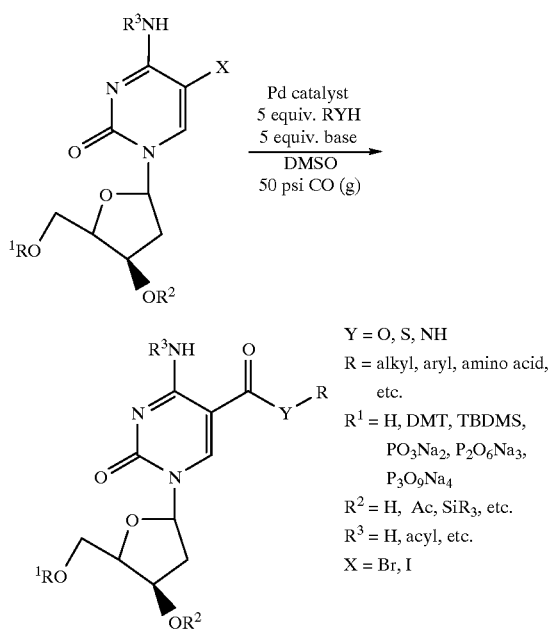

Y = O, S, NH
R = alkyl, aryl, amino acid, etc.
R¹ = H, DMT, TBDMS, PO₃Na₂, P₂O₆Na₃, P₃O₉Na₄
R² = H, Ac, SiR₃, etc.
R³ = H, acyl, etc.
X = Br, I Specific Scheme:

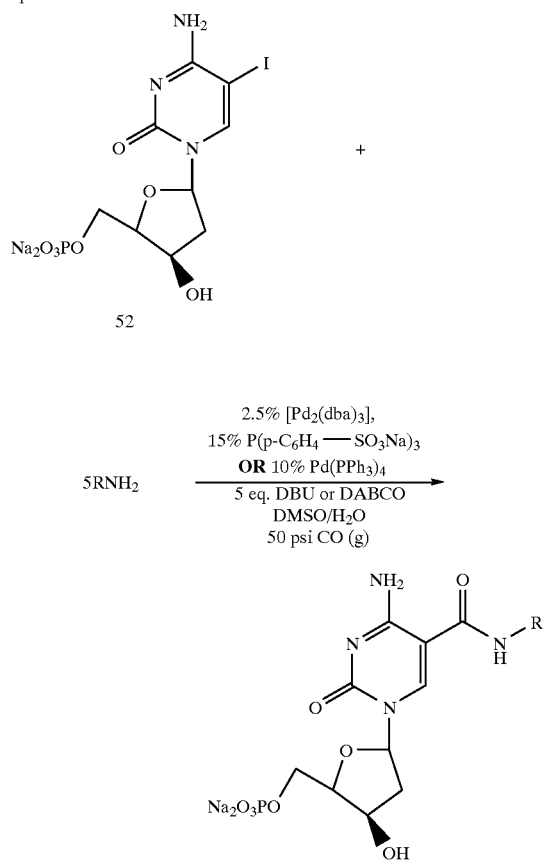

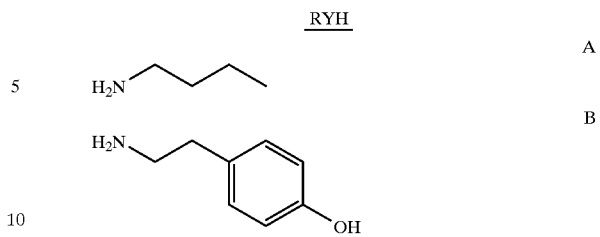

TABLE IV

Summary of 2'-deoxycytidine carboxyamidation products.

| Entry | Starting material | RNH₂ | Product ID | Isolated Yield (%) |
|---|---|---|---|---|
| 1[b] | 52 | A | 53 | 26 |
| 2[a] | 52 | B | 54 | 20 |

[a]Nucleotide (0.1 mmol), RNH₂ (0.5 mmol), Pd₂(dba)₃ (2.5 μmol), P(p-C₆H₄—SO₃Na)₃ (0.015 mmol), DABCO (0.7 mmol), DMSO (0.5 mL).
[b]Nucleotide (0.1 mmol), RNH₂ (0.5 mmol), Pd(PPh₃)₄ (0.01 mmol), DBU or DABCO (0.5 mmol), DMSO:H₂O 93:7 (0.5 mL).

Compound 53. 5-(N-butylcarboxyamide)-2'-deoxycytidine monophosphate. ¹H NMR (D₂O) δ 0.90 (t, J=7.3 Hz, 3H), 1.35 (m, 2H), 1.58 (m, 2H), 2.30 (m, 1H), 2.52 (m, 1H), 3.31 (m, 2H), 4.11 (m, 2H), 4.26 (m, 1H), 4.54 (m, 1H), 6.22 (m, 1H), 8.41 (s, 1H).

Compound 54. 5-[N-(2-[4-hydroxyphenyl]ethyl)carboxyamide]-2'-deoxycytidine monophosphate. ¹H NMR (D₂O) δ 2.27 (m, 1H), 2.41 (m, 1H), 2.82 (m, 2H), 3.51 (m, 2H), 3.90 (m, 2H), 4.19 (m, 1H), 4.50 (m, 1H), 6.16 (m, 1H), 6.83 (d, J=8.3 Hz, 2H), 7.16 (d, J=8.3 Hz, 2H), 8.19 (s, 1H).

EXAMPLE 6

Determination of Antiviral Efficacy and Cellular Toxicity

This example demonstrates the ability of nucleotides of the invention to inhibit cytopathologic effects associated with human cytomagalovirus (CMV) infection. The experimental drugs of this example will be referred to as CT1146-26 and CT1146-28. CT1146-26 is Compound 47 and has the following structure:

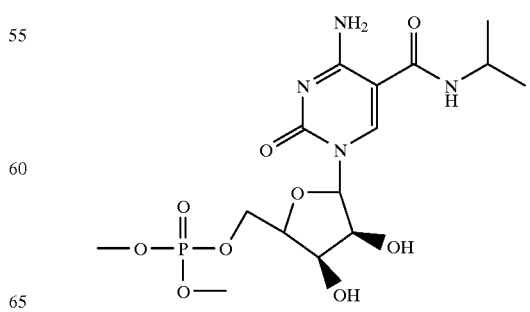

CT1146-28 is Compound 45 and has the following structure:

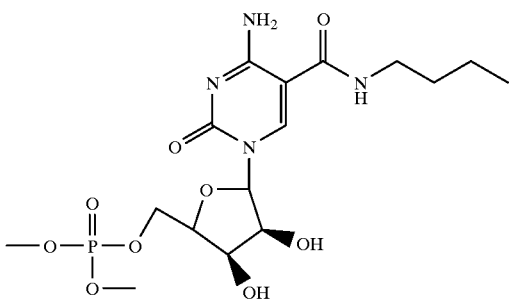

Assay methodology and preliminary results are provided in the following sections.

Cell Isolation and Tissue Culture

Newborn human foreskins were obtained immediately post-circumcision and placed in minimal essential medium (MEM) supplemented with vancomycin, fungizone, penicillin and gentamycin (all present at standard concentrations) and maintained for four hours under tissue culture conditions (37° C., 5% $CO_2$). Supplemented MEM was then removed and the foreskin material macerated. Tissue fragments were then washed exhaustively (using supplemented MEM) to remove residual erythrocyte contamination.

The erythrocyte-free cell fragments were then exposed to trypsin solution (0.25%) for 15 min with continuous stirring. Tissue fragments were then allowed to settle out of suspension and the supernatant collected and passed through sterile cheesecloth into a flask containing MEM and 10% fetal bovine serum (FBS). The cheesecloth was washed with an additional volume of MEM containing 10% FBS (The flask containing MEM and 10% FBS was maintained on ice throughout the trypsinization procedure). The trypsinization procedure was repeated using fresh trypsin solution, until no additional cell removal from tissue fragments was observed. Cells removed by this process are predominantly human foreskin fibroblasts (HFF).

Cells contained in MEM with 10% FBS were pelleted by centrifugation ($\approx$1000 RPM, 4° C., 10 min), the supernatant discarded and the pelleted cells suspended in a minimal volume of MEM with 10% FBS. HFF isolates were then plated into T-25 tissue culture flasks (the number of primary culture flasks used was based on the volume of the recovered cell pellet). HFF isolates were then maintained under tissue culture conditions (37° C., 5% $CO_2$) until confluent. Primary cultures of HFF were sequentially expanded into larger format culture flasks using standard tissue culture procedures. HFF were maintained in the presence of vancomycin and fungizone through passage four.

Cytotoxicity Assay: $IC_{50}$ Determination

HFF were seeded into 96-well tissue culture plates at a concentration of $2.5 \times 10^4$ cells/ml (100 $\mu$l MEM with 10% FBS was used as the culture medium) and maintained under tissue culture conditions for 24 H prior to experimentation. Medium from plates was then removed and 100 $\mu$l of MEM containing 2% FBS was added to all but the first row of cells in the 96-well plate. To the first row of each 96-well plate, 125 $\mu$l of control media or experimental drug CT1146-26 or CT1146-28 (initial concentration determined by the overall concentration range desired) was added in triplicate wells. Medium alone was added to both cell and virus control wells. The contents of the first row of wells were then serially diluted (1:5) across the remaining rows of the plate (25 $\mu$l volume transfer well to well, with intermediate mixing, using a Cetus liquid handling machine). Following dilution, 100 $\mu$l of CMV (2500 PFU/well final concentration) in MEM with 2% FBS was added to each well of the 96-well plate, except for wells containing cell controls. Cell control wells received an additional 100 $\mu$l of MEM with 2% FBS. The 96-well plates were then incubated under tissue culture conditions (14 day total incubation period for CMV treated HFF in 2% FBS containing MEM; media addition to cultures was made as appropriate).

Following the incubation period, medium was removed from all wells and the cells stained with 0.1% crystal violet solution for 30 min followed by several wash cycles to remove residual stain. The crystal violet stained plates were then allowed to air dry for 24 H prior to reading well absorbance values (620 nm) using a Skatron plate reader. Cellular viability and corresponding $IC_{50}$ values were determined based on absorbance values for control and experimental drug treated cells relative to control cells which were not exposed to virus. $IC_{50}$ values (50% inhibitory concentration) for experimental drugs are determined as the concentration of drug required to inhibit cellular proliferation by 50%.

Plaque Reduction Assay Using Semi-Solid Overlay: $EC_{50}$ Determination

HFF are plated into 6-well tissue culture plates and maintained under tissue culture conditions for approximately two days prior to use. On the date of assay, experimental drug solutions are prepared as 2x concentrations in 2x MEM. Serial dilutions of experimental drug are then performed (1:5) using 2x MEM. The approximate concentration range for experimental agents being 200 to 0.06 $\mu$g/ml. Each drug or control solution was then diluted 1:1 with 0.8% agarose solution. Following dilution with agarose solution, the final experimental drug concentration range was 100 to 0.03 $\mu$g/ml, with a final agarose overlay concentration of 0.4%. Viral material (CMV) was diluted in MEM with 10% FBS to yield a concentration of virus producing 20–30 plaques per well.

Media was removed from HFF cultures and 200 $\mu$l of virus containing media was added to each well (200 $\mu$l of MEM was added to control wells containing cells not exposed to virus) of each 6-well plate. The assay plates were then incubated for 1 H with shaking every 15 min. Aliquots (2 ml) of agarose/experimental drug mixture were then applied in duplicate to appropriate wells in 6-well culture plates. Control groups received 2 ml aliquots of MEM/agarose in a 1:1 dilution. Plates containing HFF and the various treatment groups were then incubated under tissue culture conditions for 14 days. On days 4 and 8, an additional 1 ml of 1:1 2x MEM:agarose mixture was added to each well.

Following incubations, HFF were stained for 4–6 H with a 1.5% solution of neutral red. The neutral red/agarose/MEM mixture is aspirated and viral plaques counted using a 10x steriomicroscope. $EC_{50}$ values (50% effective concentration) for each experimental drug are then determined as the concentration of experimental drug required to inhibit viral cytopathogenicity by 50%.

The Selectivity Index (SI) for each drug treatment was also determined (SI=$IC_{50}/EC_{50}$). Increasing efficacy of experimental drug in the absence of equivalent cytotoxicity of the drug, will result in increasing SI ratios (ie. A candidate compound with an $IC_{50}$ of 1 $\mu$g/ml and an $EC_{50}$ of 0.01 $\mu$g/ml will have an SI=100; Conversely a candidate compound with an $IC_{50}$ of 0.01 $\mu$g/ml and an $EC_{50}$ of 1 $\mu$g/ml will have an SI=0.01).

Results

Initial studies using nucleosides CT1146-28 and CT1146-26 suggest substantive anti-viral activity with respect to CMV as shown in Table V:

TABLE V

| Compound | EC$_{50}$ ($\mu$g/ml) | IC$_{50}$ ($\mu$g/ml) | SI |
|---|---|---|---|
| CT1146-28 | <0.03 | >100 | >3333 |
| CT1146-26 | <0.03 | >100 | >3333 |

EC$_{50}$ and IC$_{50}$ values are against human cytomegalovirus (CMV)

The novel nucleosides CT1146-28 and CT1146-26 exhibit significant anti-viral activity with respect to human CMV. Given the substantive differences between effective concentrations and cytotoxicity for these agents, it is unlikely that observed results reflect de facto cellular toxicity in response to treatment with these agents.

We claim:

1. A method for the preparation of a modified nucleoside comprising the steps of:
   reacting a cytosine containing a leaving group attached to the 5- or 6-position of said cytosine with a nucleophile and carbon monoxide in the presence of a palladium catalyst; and
   isolating said modified nucleoside.

2. The method of claim 1 wherein said cytosine is 5-halo-cytosine.

3. The method of claim 2 wherein said 5-halo-cytosine is selected from the group consisting of 5-iodo-cytosine, 5-bromo-cytosine and 5-iodo-cytosine-5'-monophosphate.

4. A method for the preparation of a modified nucleoside comprising the steps of:
   reacting a uracil containing a leaving group attached to the 5- or 6-position of said uracil with a nucleophile and carbon monoxide in the presence of a palladium catalyst; and
   isolating said modified nucleoside.

5. The method of claim 4 wherein said uracil is 5-halo-uracil.

6. The method of claim 5 wherein said 5-halo-uracil is selected from the group consisting of 5-iodo-uracil, 5-bromo-uracil and 5-iodouracil-5'-monophosphate.

7. The method of claim 6 wherein 5-iodo-uracil is selected from the group consisting of 5'-DMT-5-iodo-2',3'-O-isopropylideneuracil and 5'-TBDMS-5-iodo-2',3'-O-isopropylideneuracil.

8. A method for the preparation of a modified nucleoside comprising the steps of:
   reacting a nucleoside starting material containing a leaving group attached to the 2-, 5-, 6- or 8-position of said nucleoside starting material with a nucleophile and carbon monoxide in the presence of a palladium catalyst wherein said nucleophile is selected from the group consisting of an amine, alcohol and thiol; and
   isolating said modified nucleoside.

9. The method of claim 8 wherein said nucleophile has the formula RYH, wherein,
   Y is selected from the group consisting of O, S, NH and NR'; and
   R and R' are independently selected from the group consisting of a C1–C20 alkyl (straight chain or branched), C2–C20 alkenyl (straight chain or branched), aryl and an amino acid, wherein R and R' can optionally be part of a cyclic structure which can be aromatic, aliphatic or heterocyclic.

10. The method of claim 9 wherein R and R' are substituted with a functional group independently selected from the group consisting of an amide, ester, nitrile, nitro, urea halide, cyanate, alcohol, amine, ether, thiol and aryl.

11. The method of claim 9 wherein,
    Y is selected from the group consisting of O, S, and NH; and
    R is $(CH_z)_m(CH_3)_n$, wherein z is 0, 1, or 2; m is 0–19; n is 0, 1, 2, or 3; and wherein one or more of the H are optionally substituted with =O, —OH, =NH, NH$_2$, +NMe$_3$Cl, or an amino acid.

12. The method of claim 9 wherein said nucleophile is selected from the group consisting of:

-continued

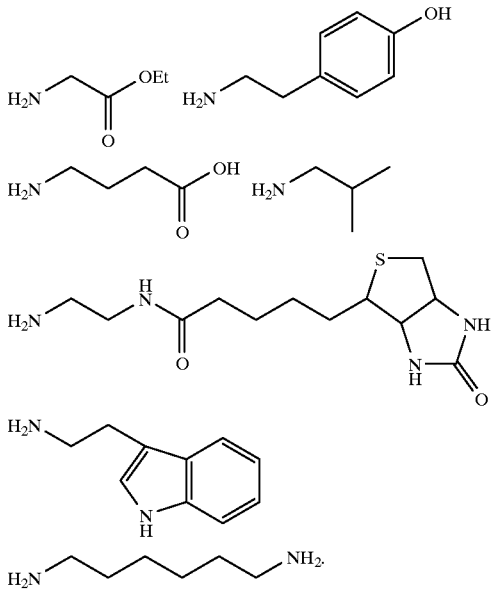

13. A method for the preparation of a modified nucleoside comprising the steps of:
reacting a nucleoside starting material containing a leaving group attached to the 2-, 5-, 6- or 8-position of said nucleoside starting material with a nucleophile and carbon monoxide in the presence of a palladium catalyst of the formula $PdL_3$ or $PdL_4$, wherein L is selected from the group consisting of $P(C_6H_5)_3$, $P(p-C_6H_4SO_3Na)_3$, $(o-tol)_3P$, $CH_3CN$, DMSO, N,N-dimethylformamide (DMF),

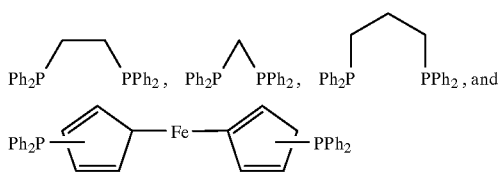

and
isolating said modified nucleoside.

14. The method of claim 13 wherein said palladium catalyst is $Pd(P(C_6H_5)_3)_4$ or $P(p-C_6H_4SO_3Na)_3$.

15. A method for the preparation of a modified nucleoside comprising the steps of:
reacting a nucleoside starting material containing a leaving group attached to the 2-, 5-, 6- or 8-position of said nucleoside starting material with a nucleophile and carbon monoxide in the presence of a palladium catalyst; wherein said leaving group is selected from the group consisting of a halogen, acetate, trifluoroacetate, tosylate, methylsulfonate, trifluoromethyl sulfonate, boronic ester and boronic acid; and
isolating said modified nucleoside.

16. The method of claim 15 wherein said leaving group is a halogen.

17. A method for the preparation of a modified nucleoside comprising the steps of:
reacting a nucleoside starting material containing a leaving group attached to the 2-, 5-, 6- or 8-position of said nucleoside starting material with a nucleophile and carbon monoxide in the presence of a palladium catalyst, in a solvent selected from the group consisting of THF, water, acetonitrile, dioxane, acetone, ethyl acetate, benzene, dimethyl formamide, dimethyl acetamide, dimethyl sulfoxide, hexamethylphophoramide, and hexamethylphosphoroustriamide; and
isolating said modified nucleoside.

18. A compound selected from the group consisting of:

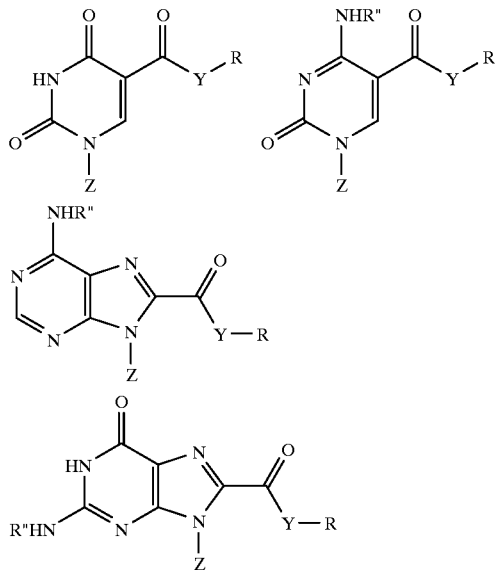

wherein,
Y is selected from the group consisting of O, S, NH and NR'; and
R and R' are independently selected from the group consisting of C1–C20 alkyl (straight chain or branched), C2–C20 alkenyl (straight chain or branched), aryl, heterocyclic, natural amino acids and unnatural amino acids, wherein R and R' can optionally be part of a cyclic structure which can be aromatic, aliphatic, or heterocyclic;
R" is selected from the group consisting of H and acyl; and
Z is selected from the group consisting of a ribose, deoxyribose, dideoxyribose, and any combination of 2', 3', and 5' modifications thereof.

19. A compound of claim 18 wherein,
Y is selected from the group consisting of O, S, and NH;
R is $(CH_2)_m(CH_3)_n$, wherein z is 0, 1, or 2; m is 0–19; n is 1, 2, or 3; and wherein one or more of the H are optionally substituted with =O, —OH, =NH, $NH_2$, $+NMe_3Cl$,

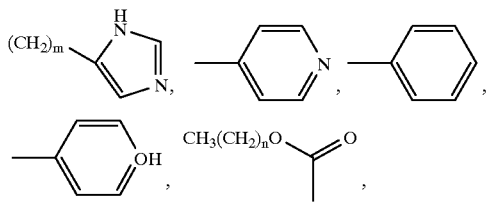

-continued
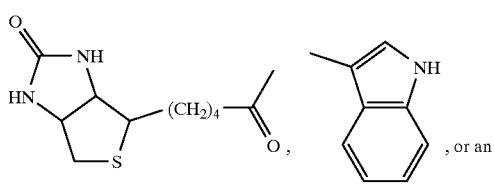, or an amino acid.
20. A compound of claim 18 selected from the group consisting of
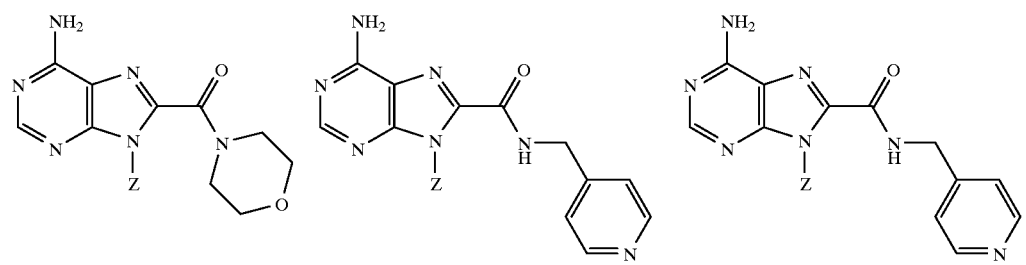
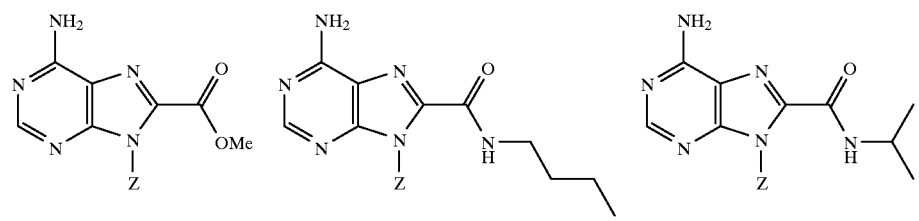
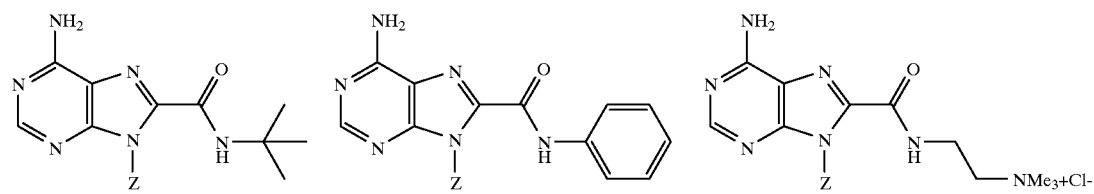
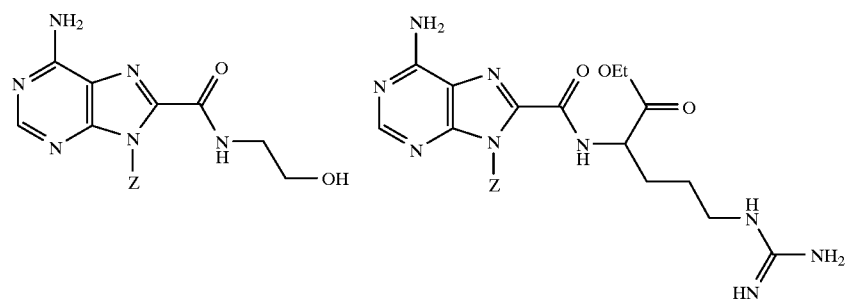
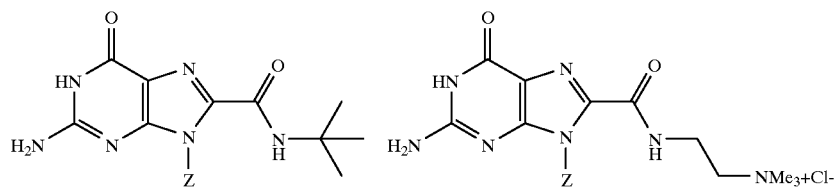

43
-continued
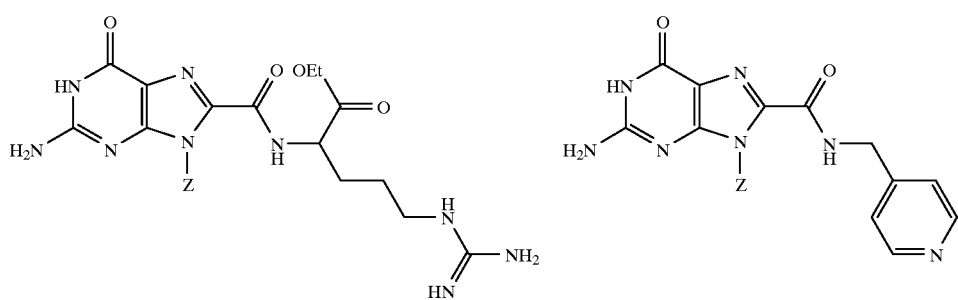
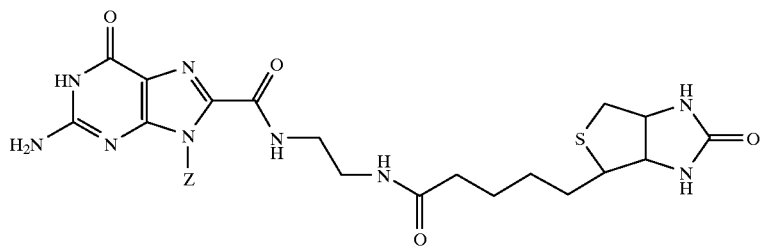
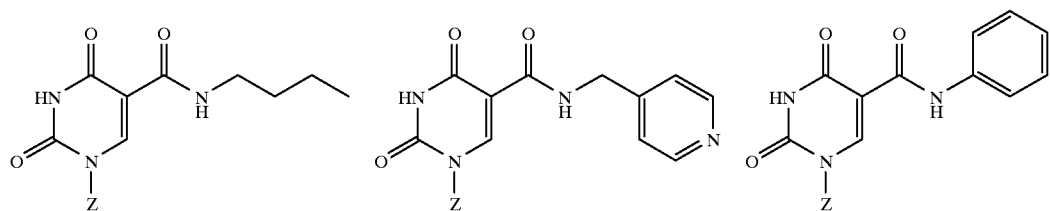
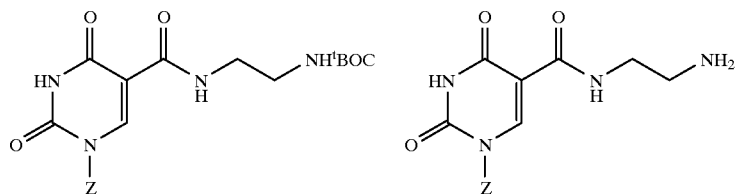
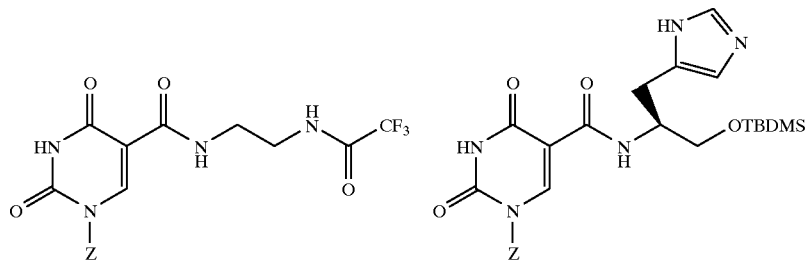
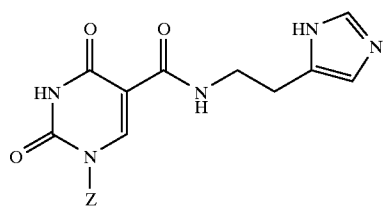
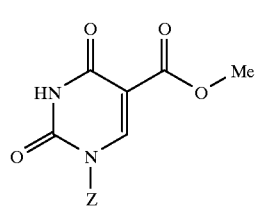
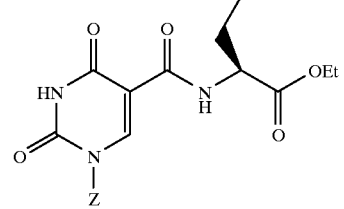

45
-continued
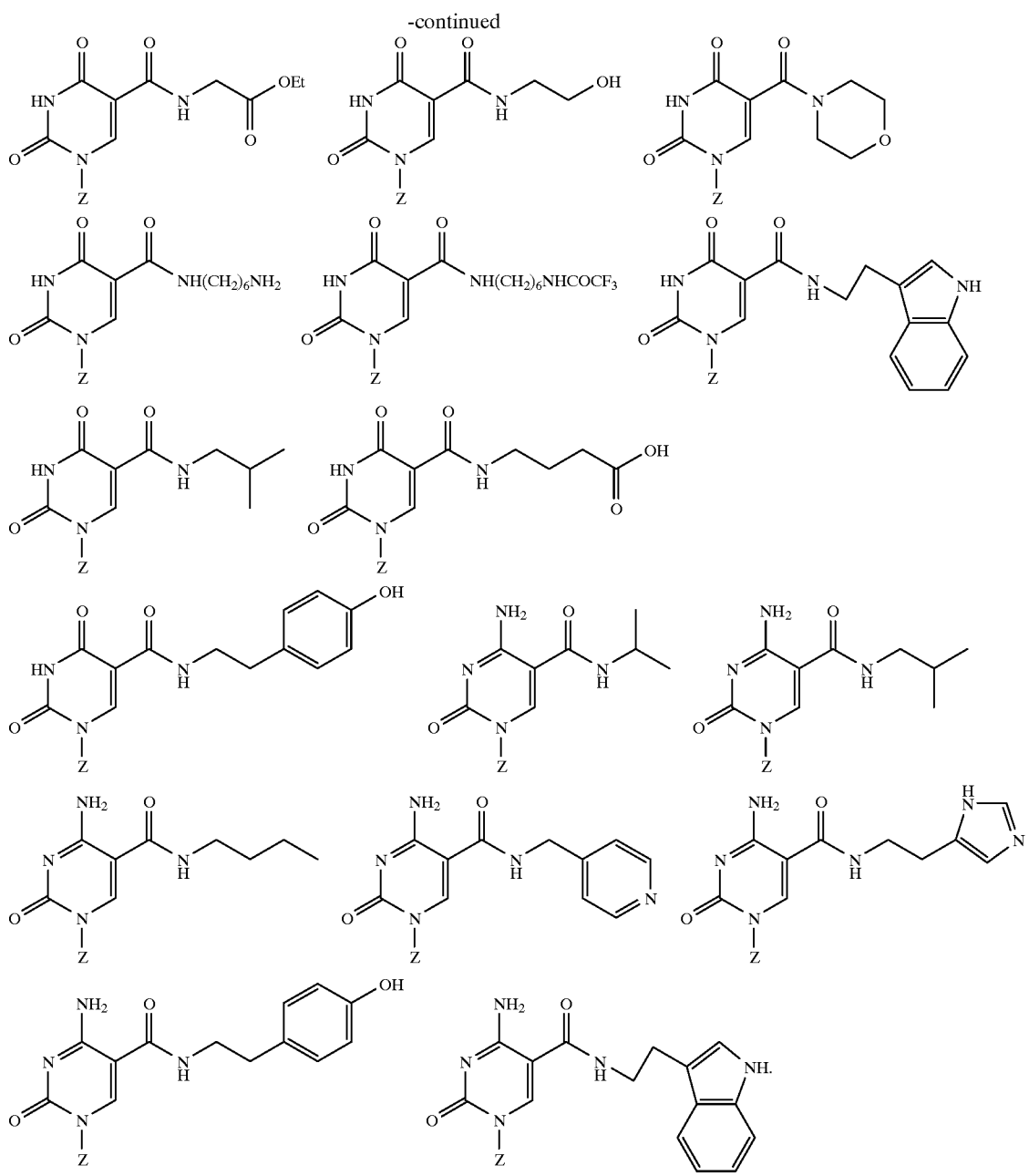
46
21. A compound of claim 18 selected from the group consisting of
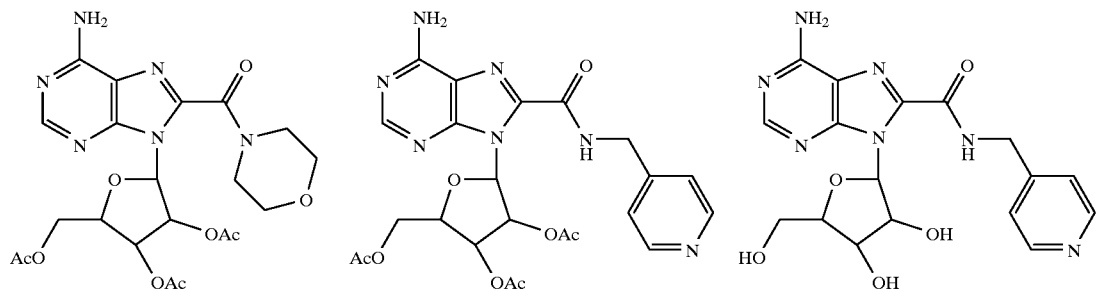

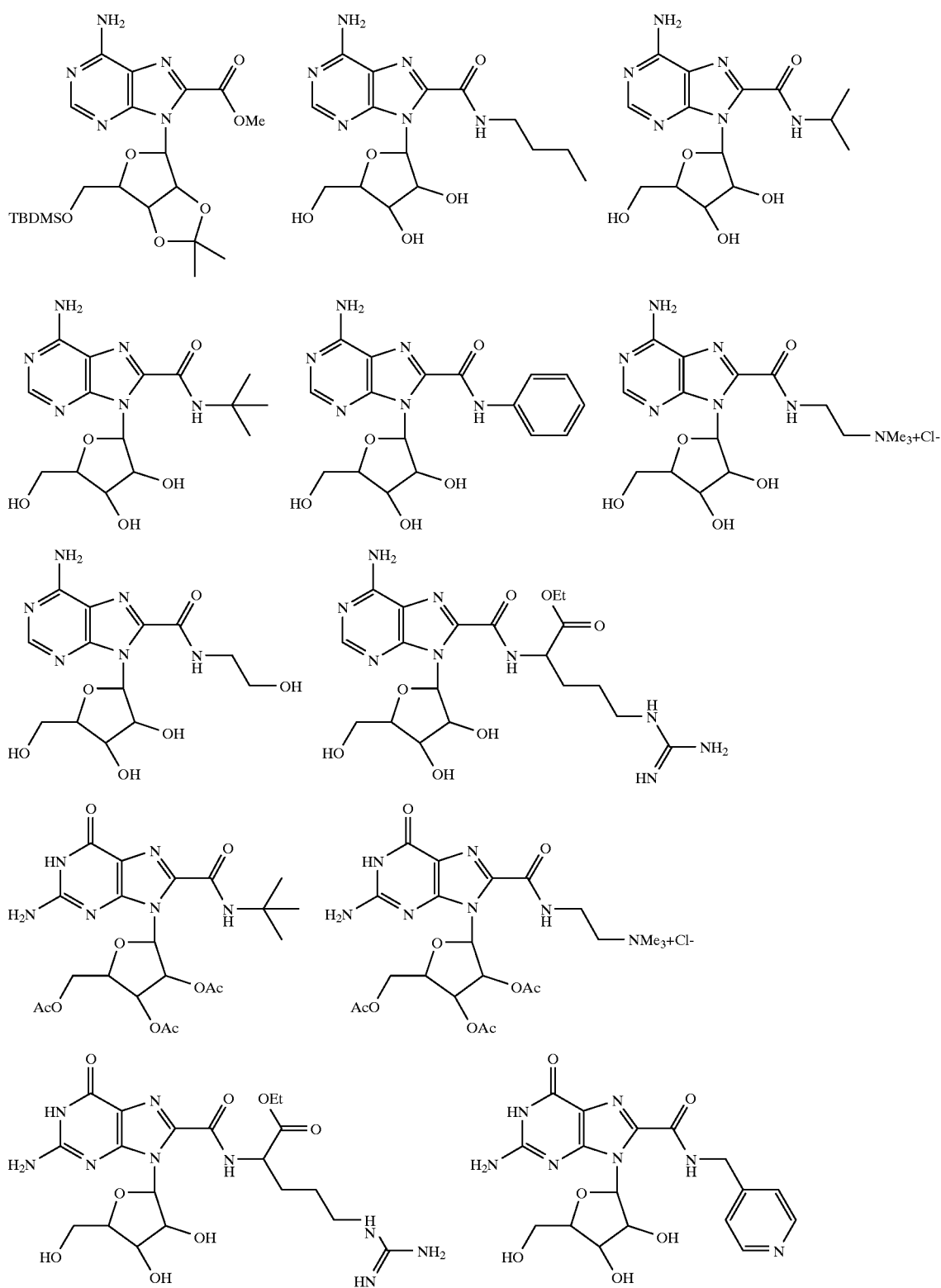

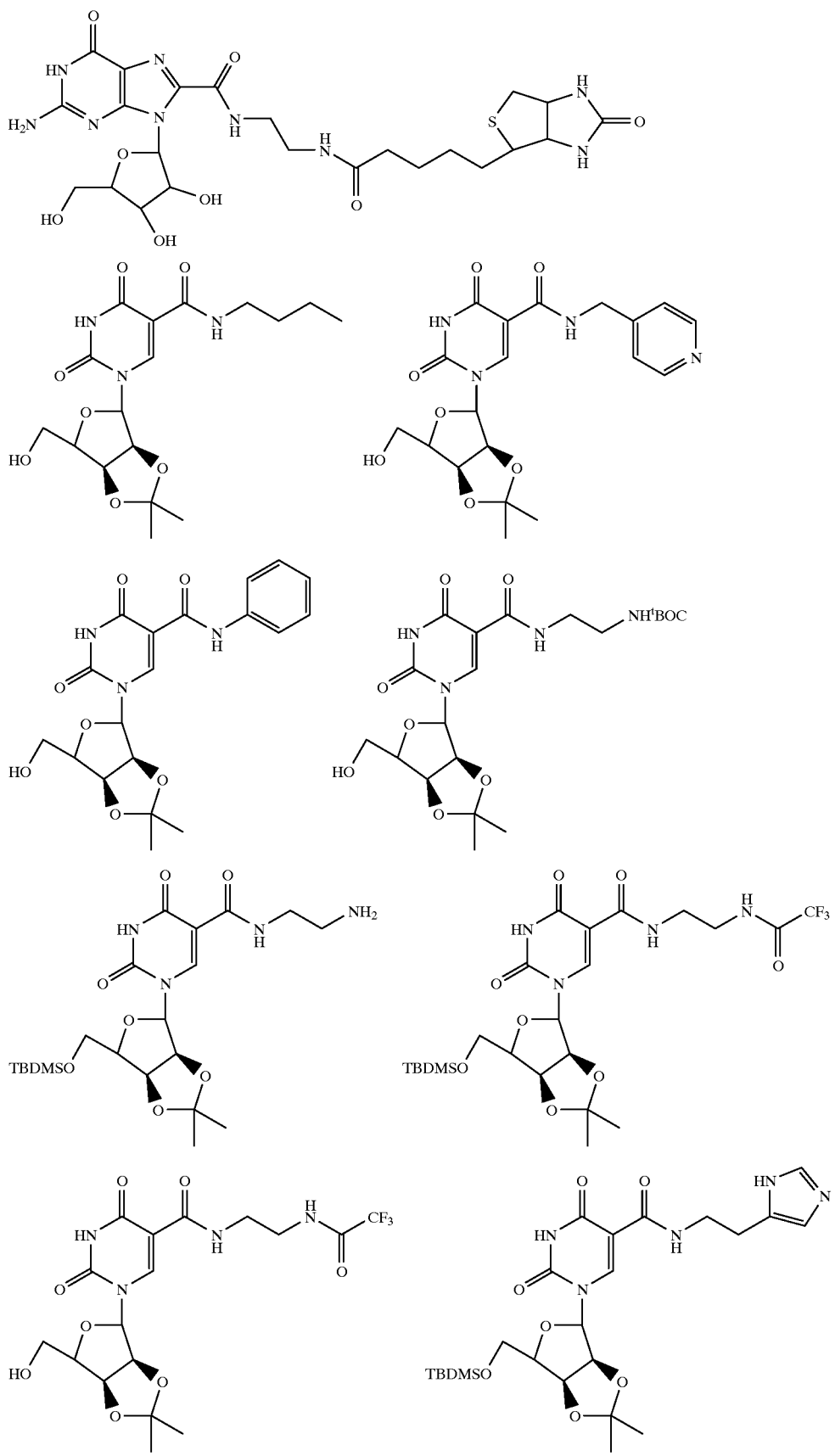

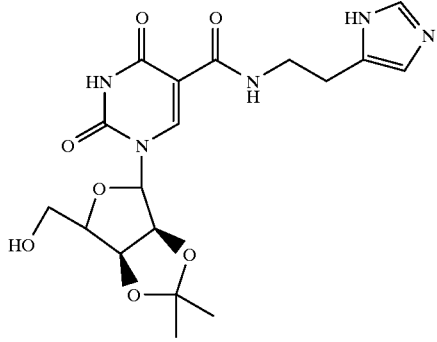
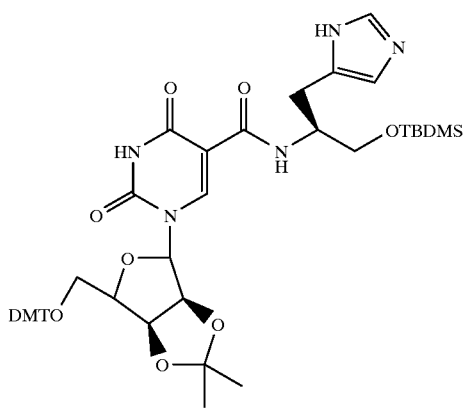
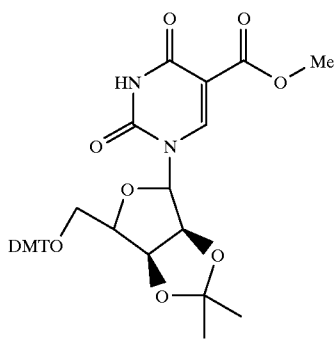
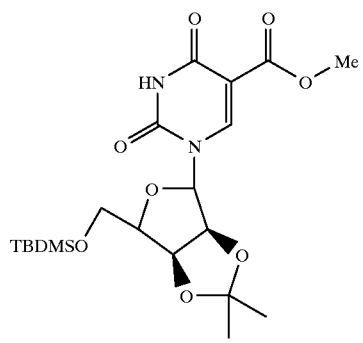
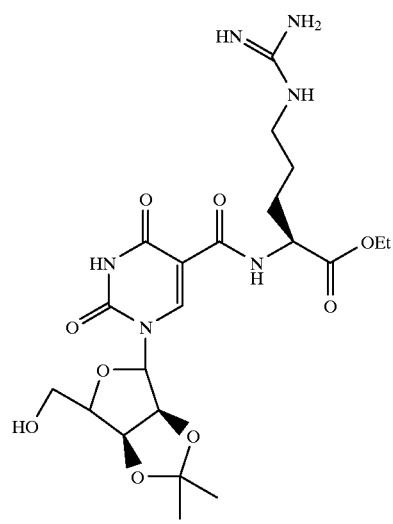
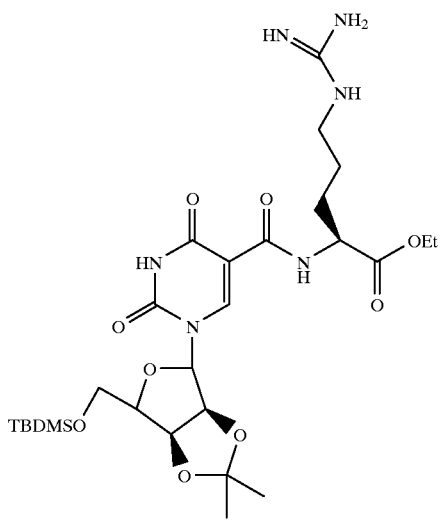
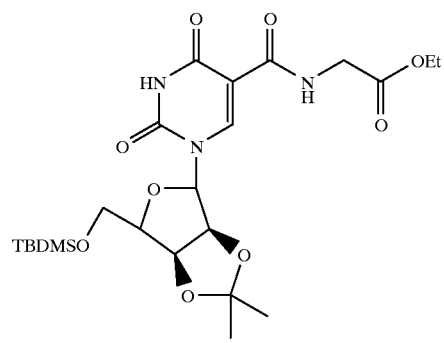

53
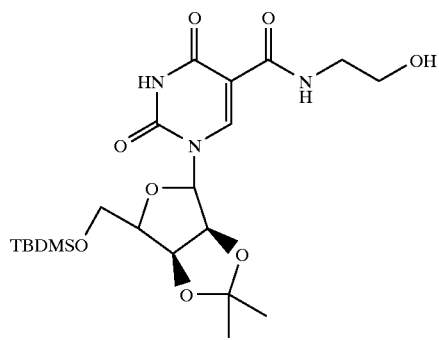
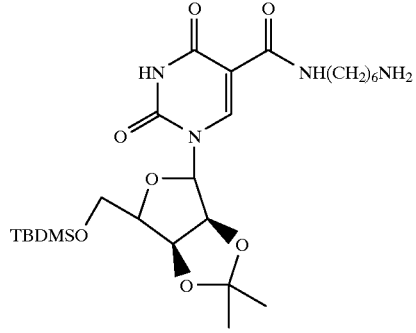
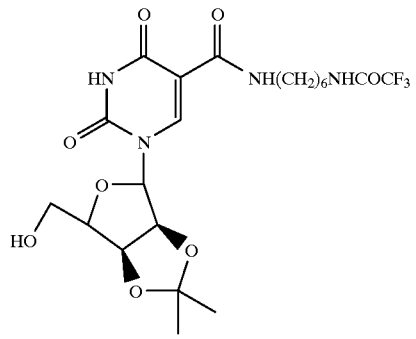
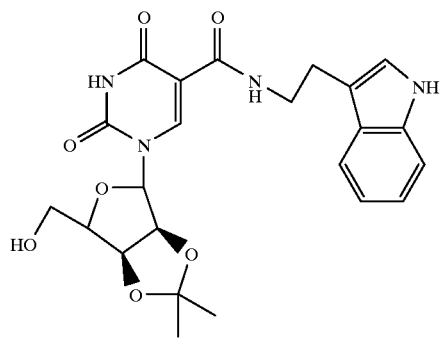
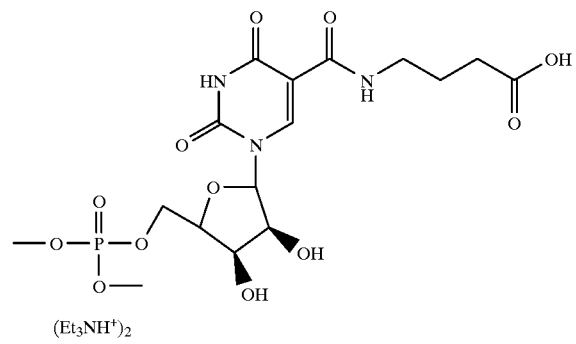
54
-continued
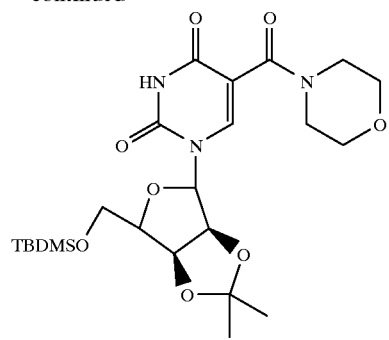
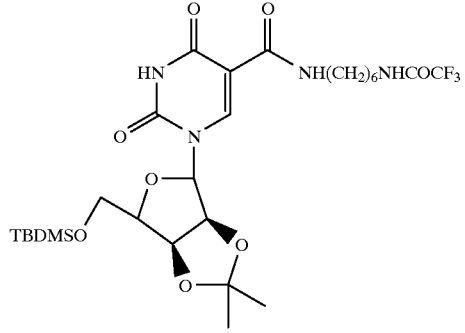
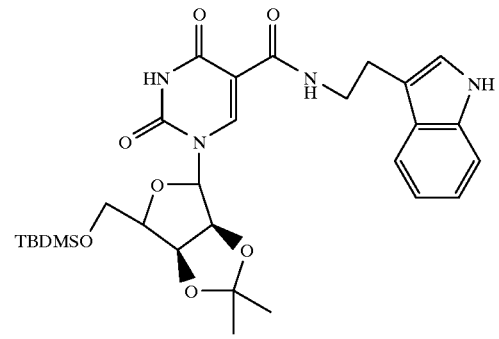
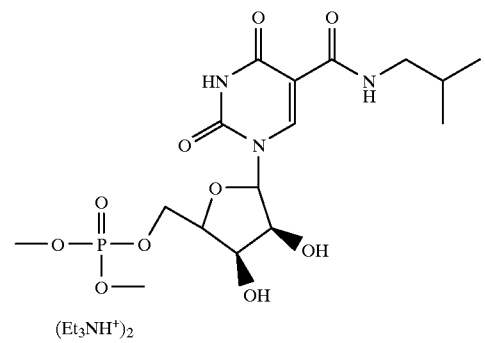
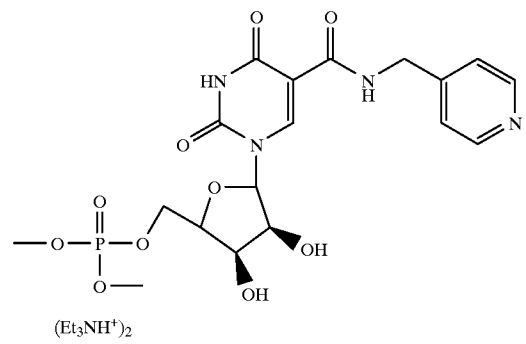

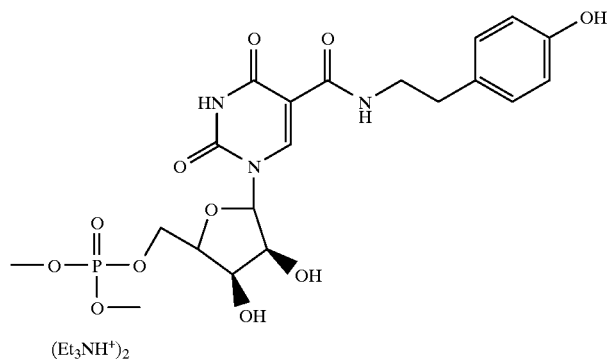
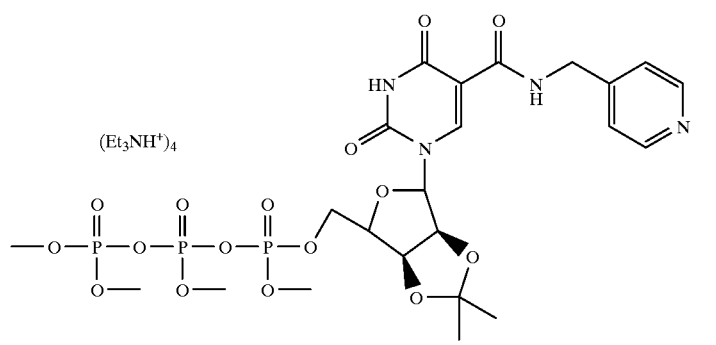
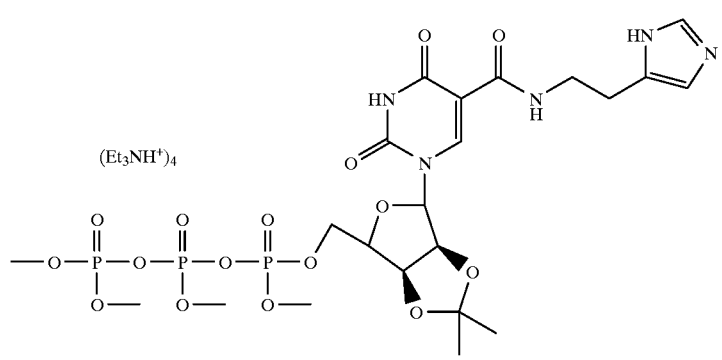
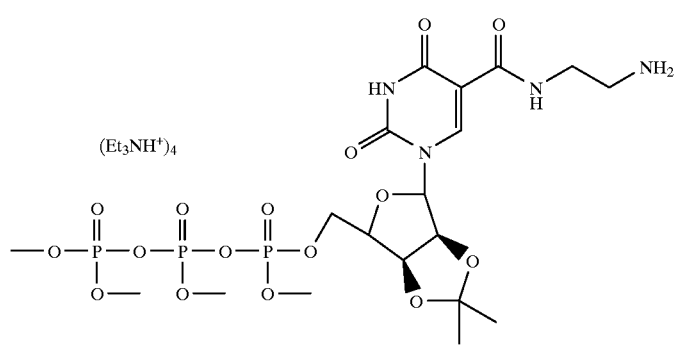

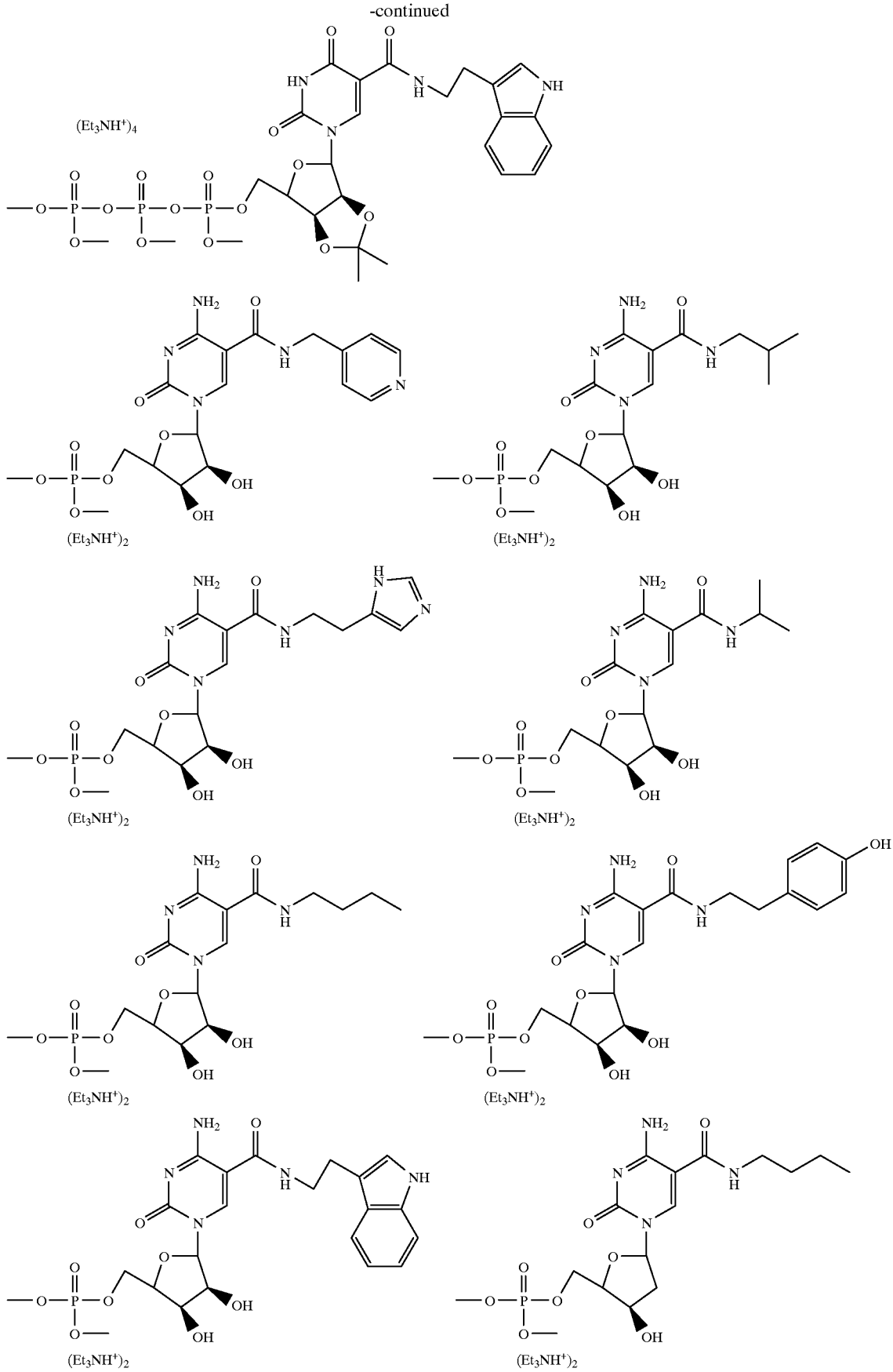

-continued

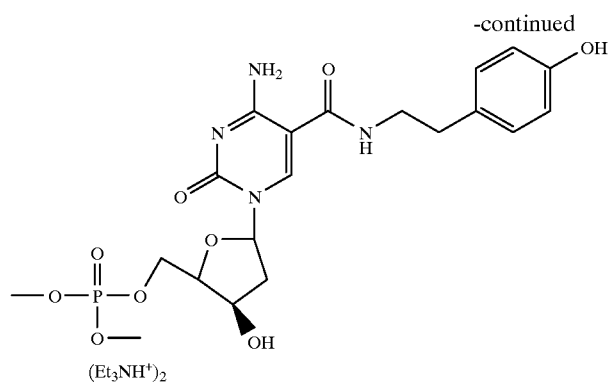

22. The compound of claim 18 incorporated as part of a oligonucleotide.

23. The compound of claim 22 wherein said oligonucleotide is a ribonucleic acid.

24. The compound of claim 22 wherein said oligonucleotide is a deoxyribonucleic acid.

25. A method for inhibiting viral activity comprising administering to a patient a therapeutically effective amount of a compound of claim 18.

26. The method of claim 25 wherein cytomegalovirus activity is inhibited.

27. The method of claim 25 wherein Y is NH and R is a C1–C20 alkyl.

28. The method of claim 25 wherein said compound is selected from the group consisting of

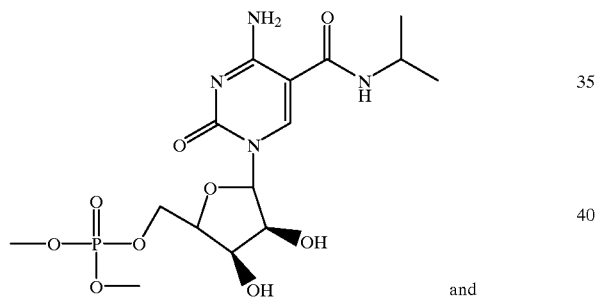

and

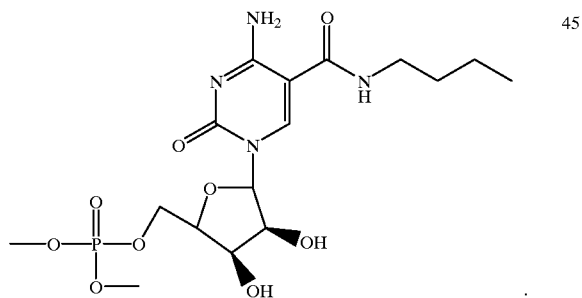

.

* * * * *